(12) United States Patent
Batiste

(10) Patent No.: US 11,672,640 B2
(45) Date of Patent: *Jun. 13, 2023

(54) THROMBECTOMY FILTER AND METHOD FOR PERFORMING A THROMBECTOMY

(71) Applicant: Stanley Batiste, Granite Bay, CA (US)

(72) Inventor: Stanley Batiste, Granite Bay, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/879,666

(22) Filed: May 20, 2020

(65) Prior Publication Data

US 2020/0375717 A1 Dec. 3, 2020

Related U.S. Application Data

(63) Continuation of application No. 15/486,199, filed on Apr. 12, 2017, now abandoned, which is a continuation of application No. 14/819,258, filed on Aug. 5, 2015, now abandoned, which is a
(Continued)

(51) Int. Cl.
| | | |
|---|---|---|
| *A61F 2/01* | (2006.01) | |
| *A61M 25/00* | (2006.01) | |
| *A61M 39/10* | (2006.01) | |
| *A61B 17/22* | (2006.01) | |

(52) U.S. Cl.
CPC ............ *A61F 2/01* (2013.01); *A61M 25/007* (2013.01); *A61M 25/0074* (2013.01); *A61M 25/0097* (2013.01); *A61M 39/10* (2013.01); *A61B 2017/22084* (2013.01); *A61F 2/011* (2020.05); *A61F 2002/016* (2013.01); *A61F 2230/0006* (2013.01); *A61F 2230/0091* (2013.01); *A61F 2230/0093* (2013.01);
(Continued)

(58) Field of Classification Search
CPC ........ A61F 2/01; A61F 2/0103; A61F 2/0105; A61F 2/011; A61F 2/012; A61F 2/013; A61F 2/014; A61F 2002/015; A61F 2002/016; A61F 2002/018; A61F 2230/0006; A61F 2230/0091; A61F 2250/0059; A61F 2250/0067; A61B 17/221; A61B 17/22031; A61B 2017/2217; A61B 2017/22034; A61B 2017/22084; A61M 25/007; A61M 25/0074; A61M 25/0097; A61M 2025/0057; A61M 39/10
USPC ....................................................... 606/200
See application file for complete search history.

(56) References Cited

U.S. PATENT DOCUMENTS

| | | |
|---|---|---|
| 3,840,017 A | 10/1974 | Violante |
| 4,494,531 A | 1/1985 | Gianturco |
| 4,793,348 A | 12/1988 | Palmaz |

(Continued)

*Primary Examiner* — Kankindi Rwego
(74) *Attorney, Agent, or Firm* — Weide & Miller, Ltd.

(57) ABSTRACT

A vascular filter system and method are disclosed. In one embodiment, the filter system comprises a dispensing needle, a guidewire and a catheter releasably attached to a filter dispenser which stores a length of filter wire. The filter wire dispenser has a guide tube which guides the filter wire into the catheter and then into a vein during surgical implantation. The filter wire is configured to form into a predetermined shape as it is deployed from the needle. The shape of the filter wire captures blood clots in the blood stream. The filter wire may be configured with a perforated section and a non-perforated section. Perforations are in fluid communication with an inner hollow lumen in the filter wire.

14 Claims, 21 Drawing Sheets

Related U.S. Application Data continuation-in-part of application No. 12/012,136, filed on Jan. 30, 2008, now Pat. No. 9,387,062.

(60) Provisional application No. 62/321,620, filed on Apr. 12, 2016, provisional application No. 60/898,939, filed on Jan. 31, 2007.

(52) U.S. Cl.
CPC ............... *A61F 2250/0059* (2013.01); *A61F 2250/0067* (2013.01); *A61M 2025/0057* (2013.01)

(56) References Cited

U.S. PATENT DOCUMENTS

| | | | |
|---|---|---|---|
| 5,108,418 | A | 4/1992 | Lefebvre |
| 5,129,910 | A | 7/1992 | Phan |
| 5,188,616 | A | 2/1993 | Nadal |
| 5,375,612 | A | 12/1994 | Cottenceau et al. |
| 5,415,630 | A | 5/1995 | Gory |
| 5,476,450 | A * | 12/1995 | Ruggio ............... A61M 1/85 604/35 |
| 5,531,788 | A | 7/1996 | Dibie |
| 5,549,626 | A | 8/1996 | Miller |
| 5,707,389 | A | 1/1998 | Louw et al. |
| 5,893,869 | A | 4/1999 | Barnhart |
| 5,895,398 | A | 4/1999 | Wensel |
| 6,007,558 | A | 12/1999 | Ravenscroft et al. |
| 6,059,825 | A | 5/2000 | Hobbs et al. |
| 6,267,777 | B1 | 7/2001 | Bosma et al. |
| 6,558,404 | B2 | 5/2003 | Tsukernik |
| 6,589,263 | B1 | 7/2003 | Hopkins |
| 6,767,353 | B1 * | 7/2004 | Shiber ............... A61B 17/22 606/159 |
| 7,131,979 | B2 | 11/2006 | DiCarlo |
| 8,961,557 | B2 * | 2/2015 | Batiste ............... A61F 2/013 606/200 |
| 9,387,062 | B2 * | 7/2016 | Batiste ............... A61F 2/01 |
| 2001/0011181 | A1 | 8/2001 | DiMatteo |
| 2001/0039450 | A1 | 11/2001 | Pavcnik et al. |
| 2002/0010481 | A1 | 1/2002 | Jayaraman |
| 2002/0116024 | A1 | 8/2002 | Goldberg et al. |
| 2002/0138097 | A1 | 9/2002 | Ostrovsky et al. |
| 2003/0018354 | A1 | 1/2003 | Roth |
| 2003/0097094 | A1 | 5/2003 | Ouriel |
| 2003/0135264 | A1 | 7/2003 | Whalen et al. |
| 2003/0208227 | A1 | 11/2003 | Thomas |
| 2004/0034383 | A1 | 2/2004 | Belson |
| 2004/0158274 | A1 | 8/2004 | WasDyke |
| 2004/0193209 | A1 | 9/2004 | Pavcnik et al. |
| 2005/0119522 | A1 | 6/2005 | Okada |
| 2005/0131451 | A1 | 6/2005 | Kleshinski et al. |
| 2006/0069405 | A1 * | 3/2006 | Schaeffer ............... A61F 2/0105 606/200 |
| 2006/0212127 | A1 * | 9/2006 | Karabey ............... A61B 17/12181 623/23.75 |
| 2006/0229668 | A1 | 10/2006 | Prestezog et al. |
| 2007/0088382 | A1 | 4/2007 | Bei |
| 2007/0112372 | A1 | 5/2007 | Sosnowski et al. |
| 2007/0270901 | A1 | 11/2007 | Shimon |
| 2008/0159771 | A1 | 7/2008 | Sakabe |
| 2009/0005803 | A1 | 1/2009 | Batiste |
| 2009/0306703 | A1 | 12/2009 | Kashkarov et al. |
| 2011/0106135 | A1 | 5/2011 | Thompson |
| 2016/0206860 | A1 * | 7/2016 | Gupta ............... A61M 25/09 |
| 2017/0119516 | A1 | 5/2017 | Batiste |

* cited by examiner

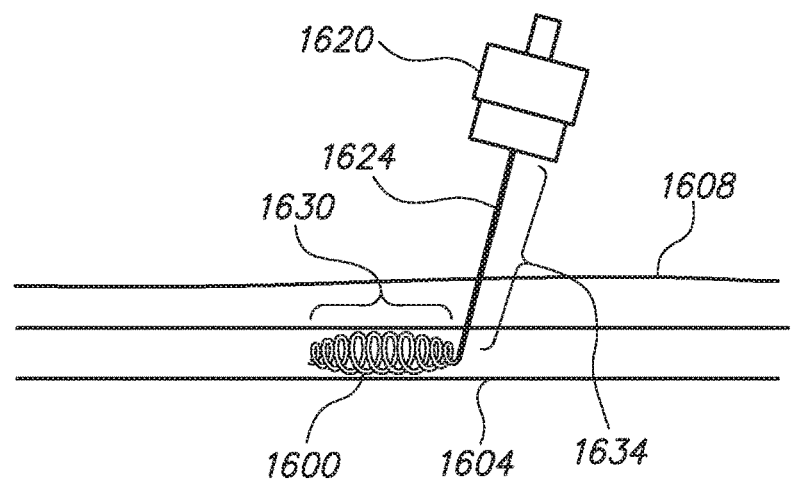
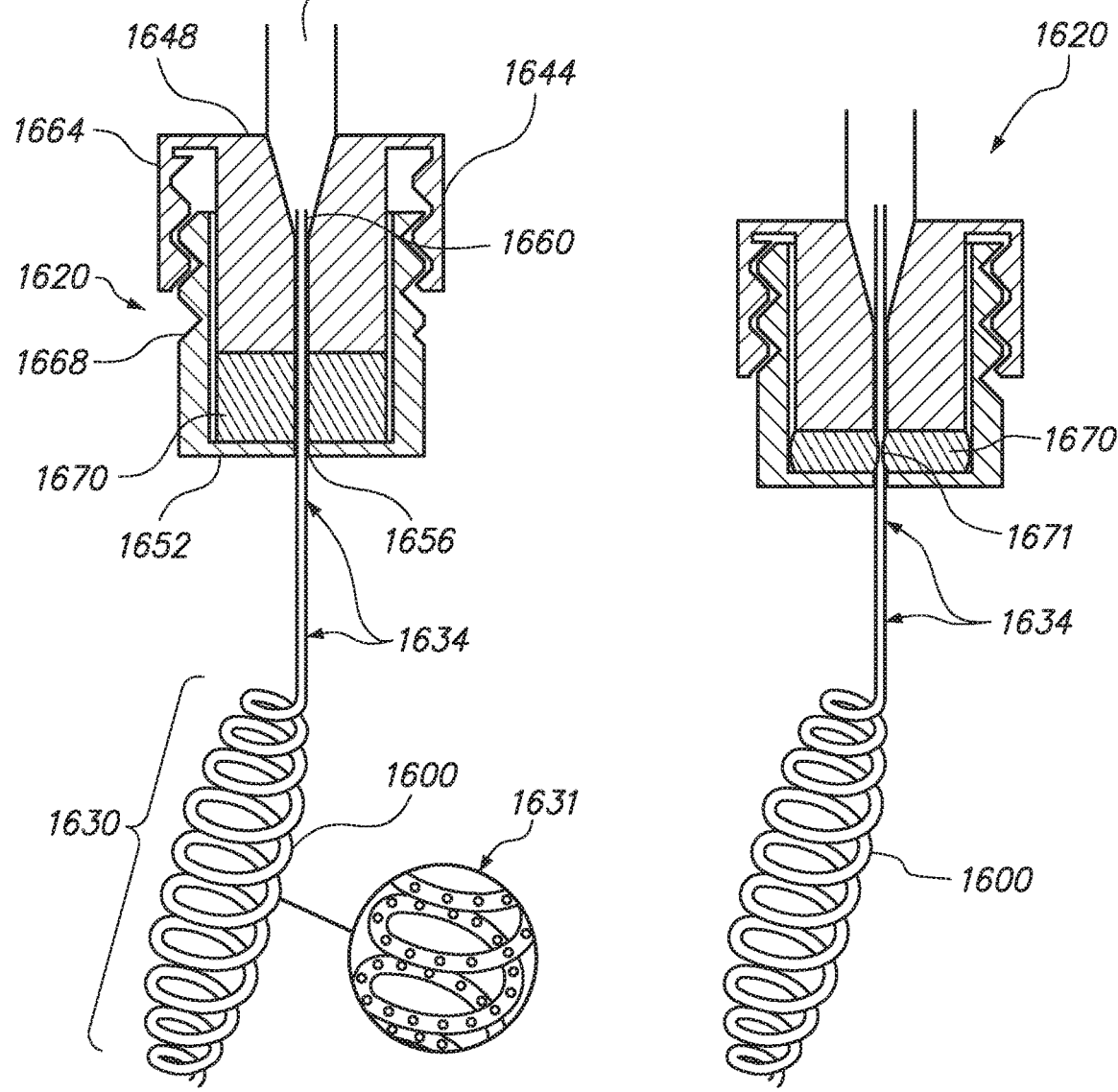
FIG. 20
FIG. 21A  FIG. 21B

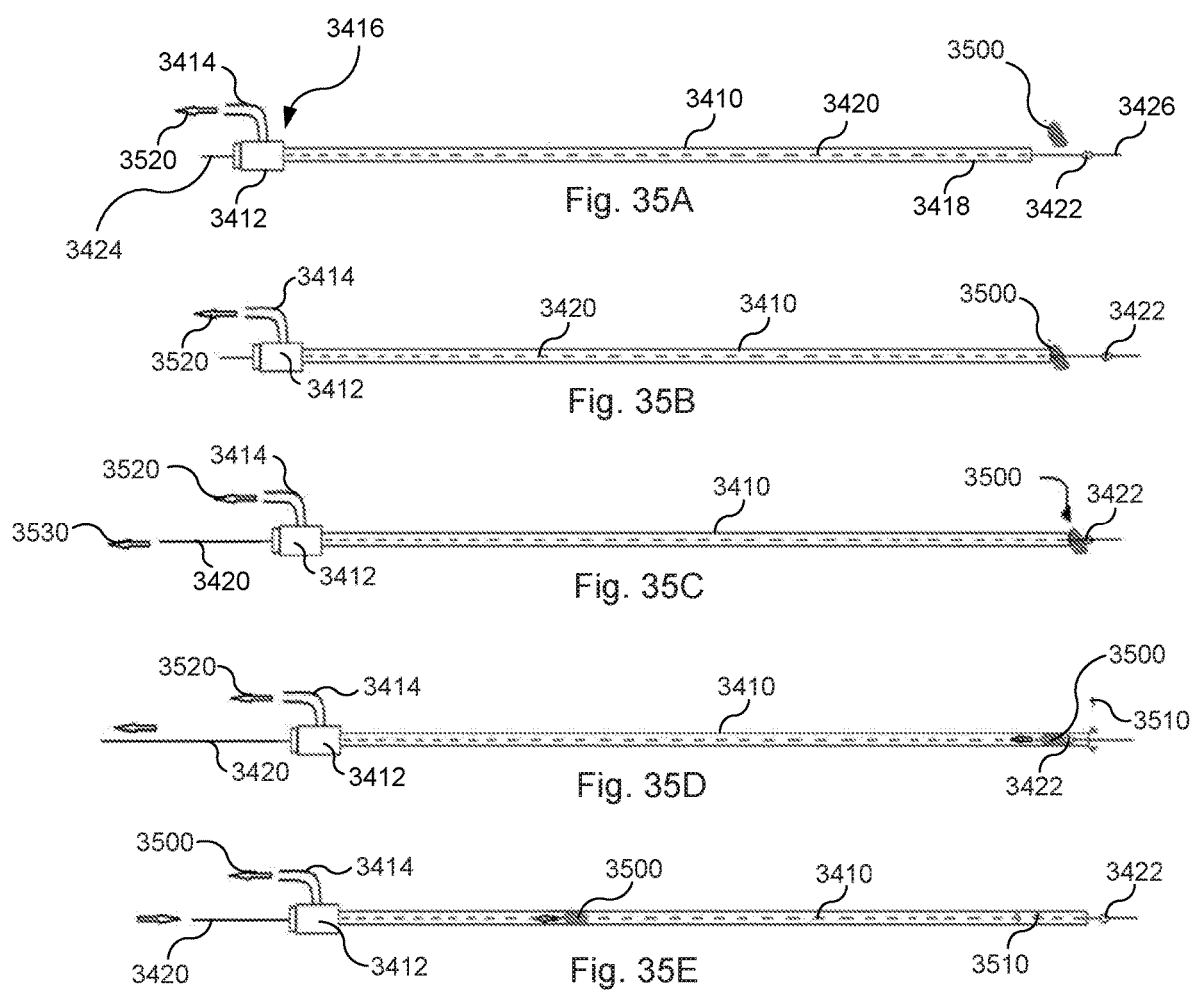

THROMBECTOMY FILTER AND METHOD FOR PERFORMING A THROMBECTOMY

CROSS REFERENCE TO RELATED APPLICATIONS

This application is a continuation of U.S. patent application Ser. No. 15/486,199 filed on Apr. 12, 2017, which claims priority to U.S. Provisional Application No. 62/321,620 which was filed on Apr. 12, 2016, and is a continuation-in-part of U.S. patent application Ser. No. 14/819,258 filed on Aug. 5, 2015, which application is a continuation-in-part of U.S. patent application Ser. No. 12/012,136 filed on Jan. 30, 2008, which claims priority to U.S. Provisional Patent Application No. 60/898,939 filed on Jan. 31, 2007 the contents of which are hereby incorporated by reference.

BACKGROUND

1. Field of the Invention

The disclosed embodiments relate to vascular filters and, in particular to surgically implanted vascular filters which capture blood clots to prevent the clots from migrating to other regions of the circulatory system.

2. Related Art

Deep vein thrombosis (DVT) is a common problem and causes significant morbidity and mortality in the United States and throughout the world. DVT is the formation of a blood clot within a deep vein, predominantly in the legs. These blood clots typically occur due to slow or reduced blood flow through the deep veins such as when the patient cannot ambulate or otherwise efficiently circulate their blood. Another cause of inefficient circulation may be due to structural damage to the veins resulting from general trauma or surgical procedures. Additionally, a blood clot may form in a deep vein due to a particular medical condition or a propensity for the patient to have a hypercoaguability state. For example, a woman on birth control who smokes has an increased risk of forming blood clots and is thus predisposed to DVT.

The result and clinical significance of DVT is when the clot breaks free from its location in the deep vein of the leg. The clot travels through the circulatory system and may eventually lodge in a location that is adverse to the patient's health. For example, the clot may dislodge from a location in the deep vein of the patient's leg and migrate through the heart and come to rest in the patient's lung causing a pulmonary embolism (PE) resulting in the restricted circulation of blood in the lungs. PE may cause sudden death for the patient. As many as 600,000 cases of clinically significant Pulmonary Embolus occur and result in approximately 200,000 deaths annually in the United States.

DVT & PE are currently prevented in several ways including anticoagulation therapy, thrombectomy, thrombolysis and inferior vena cava filter (IVC filter) placement. Anticoagulation therapy utilizes various medications that reduce the patient's propensity for forming blood clots. However, this form of therapy has the disadvantage that due to the patient's inability to form blood clots (due to the medication), there is an increased risk of excessive bleeding should the patient become injured, sustain surgical complications, or develop internal hemorrhaging.

Thrombectomy is a procedure generally performed for treatment of a PE, in which a blood clot is extracted from the vein using a surgical procedure or by way of an intravenous catheter and a mechanical suction device. This form of treatment is risky and technically very difficult because the catheter has to be steered or navigated to a specific location in order to extract the clot. Additionally, during a thrombectomy there is an increased risk of causing vascular damage due to the surgical procedure and use of various mechanical devices.

Thrombolysis is a medical technique that is performed for treatment of a PE, in which various medicines are infused into the region of the clot that subsequently causes the clot to dissolve. This form of treatment has the disadvantage that the medication may cause bleeding at other sites such as within the brain. For example, if a patient has previously had a minute non-clinical stroke, the medication used in a thrombolysis may cause a previously healed vessel to bleed within the patient's head.

IVC filter placement is usually conducted by surgically installing a filter in a large bore vein (such as the inferior vena cava) in the patient's upper abdomen. The IVC filter is placed using a large bore catheter (Introducer Catheter) introduced into the patient from the patient's jugular vein and steered to the inferior vena cava for delivery of the filter. Typically, a removable IVC filter is utilized based on FDA recommendations to remove the IVC filter once protection from PE is no longer needed. In the case where a removable filter is utilized, additional complications arise when the filter must be removed.

The removable IVC filter is generally placed for a time period of a several weeks to a few months to prevent internal vascular scaring. However, removal of the IVC filter is technically challenging and requires large bore access. In practice, the removable IVC filter is captured by first accessing a large bore vein, such as the jugular vein, using a large bore catheter to approach the filter, capturing the tip of the filter using a "snaring device" that is deployed through the large bore catheter, then pulling the filter into the catheter, and then the large bore catheter (with the filter therein) is removed from the patient. This procedure is very challenging, and requires increased patient recovery time.

Current IVC filter placement has several disadvantages such as increased costs, requires the use of special surgical procedures such as fluoroscopy or cardiology labs, requires a team (lab technician, nurse, and physician) of medical professionals, and requires a second substantially difficult surgical procedure for filter removal. Additionally, the IVC filter placement procedure requires that the patient's coagulation status be sufficient to withstand the surgical procedure. For example, if the patient has medical condition (liver failure) or is on medications that prevents their blood from clotting (i.e., using anticoagulation therapy) there is a substantial risk of excessive bleeding during the procedure. Also, existing IVC filter placement procedures are of questionable practicality for preventative placement because of the intrusive surgical procedures that must be performed to place the filter. Correspondingly, the risks (particularly filter removal) must be balanced between the need for the filter and the patient's ability to endure the surgical procedure.

Other complications may also arise from existing IVC filters. For example, despite FDA recommendations, the retrieval rate of IVC filters is very low given the complexity of the procedure to remove the filters. When the filters remain in the body, there is the possibility of filter fracturing and migrating into other parts of the body. Further, the filter may perforate the wall of the vein, and may even perforate into adjoining tissues or organs.

As a result, there is a need in the art for a vascular filter that is inexpensive, facilitates placement by a physician at a convenient patient location (bedside), allows non-intrusive removal that can be performed at any location by either a physician or trained technician while having minimal recovery time and eliminating the need to determine the coagulation status of the patient. The method and vascular filter described herein enables a physician to place and remove the filter with minimal physical intrusion and at the same time reducing risk of procedural complications for the patient.

SUMMARY

To overcome the drawbacks of the prior art and provide additional benefits and features, a vascular filter and method of filter placement is disclosed. In one embodiment, the vascular filter includes a dispensing needle releasably attached to a syringe and a filter wire dispenser. Generally, the needle has two ends, a delivery end and a coupling end. The delivery end is placed within a vein and allows filter wire to be implanted into the vein. The coupling end allows the needle to be releasably connected to a filter wire dispenser or syringe.

The filter wire dispenser stores a length of filter wire which is configured to coil upon deployment from the delivery end of the needle into a vein. The filter wire dispenser may store the filter wire as a spool or linearly, and includes a guide tube sized to insert into the needle. The guide tube is used to guide the filter wire from the dispenser into the needle.

The filter wire may be configured to coil upon deployment in a number of ways. One way is to put residual stresses, surface tensions, or both into the filter wire such that, once deployed, the filter wire will coil into a predetermined shape as defined by the stresses and surface tensions in the filter wire. The filter wire may be configured to coil into a vortex type, nested, or tangled web shape as desired. In addition, the filter wire of some embodiments may have a flexible tip to better prevent damage to the interior walls of a vein.

Once deployed a portion of the filter wire may be left protruding from the patient to allow the filter to be fixed in position. The protruding portion of the filter wire may be secured to a fixation device attached to the patient's skin. In one or more embodiments, the fixation device may have a portion configured to engage and secure the filter wire such as a protrusion.

The vascular filter, in one embodiment, is implanted by accessing a vein with a needle, attaching a filter wire dispenser storing a length of filter wire to the needle, and advancing the filter wire through the needle such that the filter wire exits the delivery end of the needle. In one or more embodiments, the filter wire has two ends, a first end and a second end. In one embodiment, the first end of the filter wire exits the dispenser first. As the filter wire exits the needle into the vein, it begins to coil, as described above, to form a vascular filter.

Once the vascular filter is fully deployed the needle may be removed. In one or more embodiments, a portion of the filter wire is left protruding out of the patient so that it may be secured to a fixation device which generally covers the exist passage of the filter wire.

In some embodiments, proper access to a vein may be verified prior to implanting the filter. One way to verify that the needle is accurately located in a vein is to attach a syringe to the needle and draw blood from the vein to confirm the needle is indeed properly within the vein. The needle is improperly placed if no blood can be drawn. Once verified, the syringe may be removed from the needle while leaving the needle in the vein. A filter wire dispenser may then be attached and the filter wire implanted subsequently.

The vascular filter may be removed when desired or when no longer needed. In one embodiment, the vascular filter is removed by removing the filter wire from its associated fixation device and drawing the filter wire out of the patient. As the filter wire is drawn out of the patient, the filter wire unwinds itself so that it may be easily removed.

In one embodiment, a vascular filter system as described herein is provided with medication infusion capability. In such an embodiment, the filter wire is configured to coil within or around the filter wire dispenser and further configured for coiled deployment from the filter wire dispenser to a patient, the filter wire comprising an open first end connected to a hub assembly. The filter wire includes an inner lumen within the filter wire in fluid communication with the open first end. The filter wire also includes a perforated section and a non-perforated section. Two or more infusion ports are in the perforated section such that the two or more infusion ports are in fluid communication with the inner lumen of the filter wire. A hub assembly is at the open first end such that the hub assembly is configured to surround at least a portion of the non-perforated section of the filter wire and selectively open and close the inner lumen to control the flow of medication into the perforated portion of the filter wire.

In one configuration, the infusion ports are holes in the perforated section of the filter wire which establish the inner lumen in fluid communication with the blood stream. The hub assembly may comprise a luer lock. In one embodiment, the hub assembly is configured to mate with a syringe to accept an administration of medication into the inner lumen of the filter wire.

Also disclosed is a vascular filter system that includes a length of filter wire having a first end and a second end. In this embodiment, the length further includes a non-perforated section at the first end with an opening at the first end that is part of an inner passageway within the filter wire. A perforated section connects the non-perforated section and the second end such that the perforated section is configured to coil to form a filter upon deployment from the delivery end of the dispensing needle. Also part of this embodiment are two or more perforations in the perforated section that are in fluid communication with the inner lumen. A hub assembly is releasable connected near the first end of the filter wire and is configured to selective open and close the inner lumen.

In one variation, the vascular filter system further comprises an antithrombogenic on at least an outer surface of the perforated section. The portion of the filter wire that is within the hub assembly may be resilient.

In one embodiment, a thrombectomy filter design provides a unique solution to the problem of DVT and PE management by lessening time and financial cost while increasing procedural efficiencies, decreasing the number of procedures and improving patient care. Currently, thrombus removal in the extremities requires pre-procedural IVC filter placement. This is to prevent pieces of the clot that may be dislodged during the procedure from traveling to the lungs. Filter placement is typically performed from jugular access in the lower neck, and the filter is place below the renal veins in the Inferior Vena Cava in the mid abdominal cavity. This leaves a patient with an entry point in the neck which is a potential site of bleeding if thrombolytic medications are given to break up the clot. Once the procedure is complete, by FDA recommendations, the filters need to be removed which can be a difficult procedure, and, in some cases, may not be possible. Patients are scheduled for filter removal typically 3 months after the initial procedure. Once the IVC filter is out the patient management is complete.

The new thrombectomy filter design uniquely combines blood filtration during the thrombectomy procedure with complete removal of the filter on procedure completion. The embodiments eliminate the need to place an IVC filter prior to the procedure and also eliminates the need for a post-procedure IVC filter removal.

Several embodiments are described within, each with the ability to provide blood filtration within the vein during the thrombectomy procedure. Embodiments of the included thrombectomy filter designs are compatible with current thrombectomy wires. An exemplary thrombectomy wire is composed of a wire segment which fits inside a catheter and has an enlarged bead shaped segment on the distal wire tip for dislodging a clot disposed at the tip of the catheter. The catheter is initially advanced into a vein containing a clot, and suction is applied to the proximal catheter tip. The suction aspirates the clot through the catheter to clear the vein. The clot may intermittently occlude the distal catheter tip. This may be cleared by drawing the wire with the bead tip into the catheter. Once cleared, the wire is then re-advanced distally to the distal tip of the catheter and clot aspiration resumes.

One embodiment of the thrombectomy filter uses the thrombectomy wire as a platform and does not change the wire function of clot clearance. The new filter design is continuous with the distal tip of the thrombectomy wire to provide protection if a clot or portion thereof is dislodged and travels within the vessel towards the heart and lungs. The filter component may be a helix shape, an umbrella shape, a vortex shape, a nested shape, and a tangled web shape, and may oppose or not oppose the inner vessel wall. This thrombectomy wire filter is placed within the thrombectomy catheter which the thrombectomy filter wire is advanced through and deployed. The wire is then used in the same fashion as the thrombectomy wire. Once the clot is removed the thrombectomy filter wire (including the filter) is removed.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The components in the figures are not necessarily to scale, emphasis instead being placed upon illustrating the principles of the invention. In the figures, like reference numerals designate corresponding parts throughout the different views.

FIGS. 12 and 13 illustrate removal of the filter dispenser and needle, wherein FIG. 12 is shown with the filter dispenser and needle being removed, and FIG. 13 is shown without the filter dispenser and needle.

FIG. 20 illustrates an infusible filter and associated hub assembly.

FIG. 21A illustrates a more detailed view of the infusible filter and hub assembly including a close up of the filter wire with infusing mechanism.

FIG. 21B illustrates the assembly of FIG. 21A with the compression element compressed to close the inner lumen of the view of the filter.

FIG. 35A, FIG. 35B, FIG. 35C, FIG. 35D, and FIG. 35E illustrate operation of an exemplary catheter and wire for a thrombectomy, shown with a clot in first, second, third, fourth, and fifth positions, respectively.

FIG. 36A and FIG. 36B illustrate a thrombectomy filter design, according to an exemplary embodiment, wherein FIG. 36A is shown without a catheter, and FIG. 36B is shown with a catheter.

DETAILED DESCRIPTION OF EMBODIMENTS

In the following description, numerous specific details are set forth in order to provide a more thorough description of the present invention. It will be apparent, however, to one skilled in the art, that the present invention may be practiced without these specific details. In other instances, well-known features have not been described in detail so as not to obscure the invention.

One of the primary concerns regarding deep vein thrombosis (DVT) is that should the thrombosis (blood clot) dislodge from the original location, the clot may travel to another region of the circulatory system and cause injury and or death to the subject. For example, if a DVT dislodges it may migrate through the heart and eventually re-lodge in the lung of the subject, thus causing a pulmonary embolism (PE) which prevents adequate circulation and respiration and can cause sudden death. By placing an intravenous filter in the common femoral vein, the blood clot is captured and prevented from migrating to vulnerable regions of the circulatory system. The filter may be placed in any vein or at any location such that the filter can capture a clot prior to causing damage to the patient. The term vein and vessel are used and defined interchangeably herein.

Figure 1:
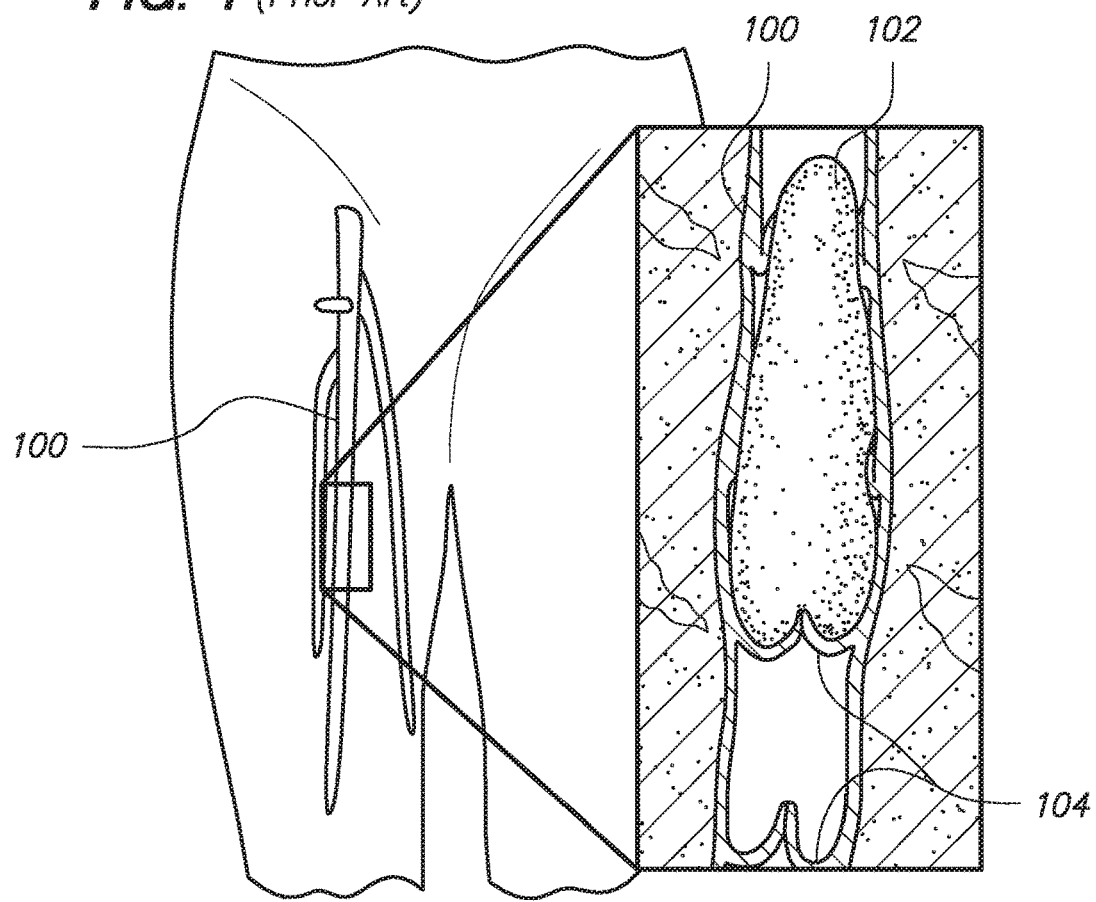
FIG. 1 illustrates a typical blood clot lodged within a femoral vein.

Referring now to the drawings, FIG. 1 illustrates a typical DVT where the common femoral vein 100 has a blood clot 102 lodged therein. As the blood clot 102 is formed there is reduced blood flow through the common femoral vein 100 because the blood clot begins to obstruct the fluid pathway. The reduced blood flow produces an environment that facilitates clot formation. In particular, as the blood flow is reduced, blood begins to coagulate in the chambers of the vascular valves 104, and, as a result, the blood clot 102 increases in size.

Figure 2:
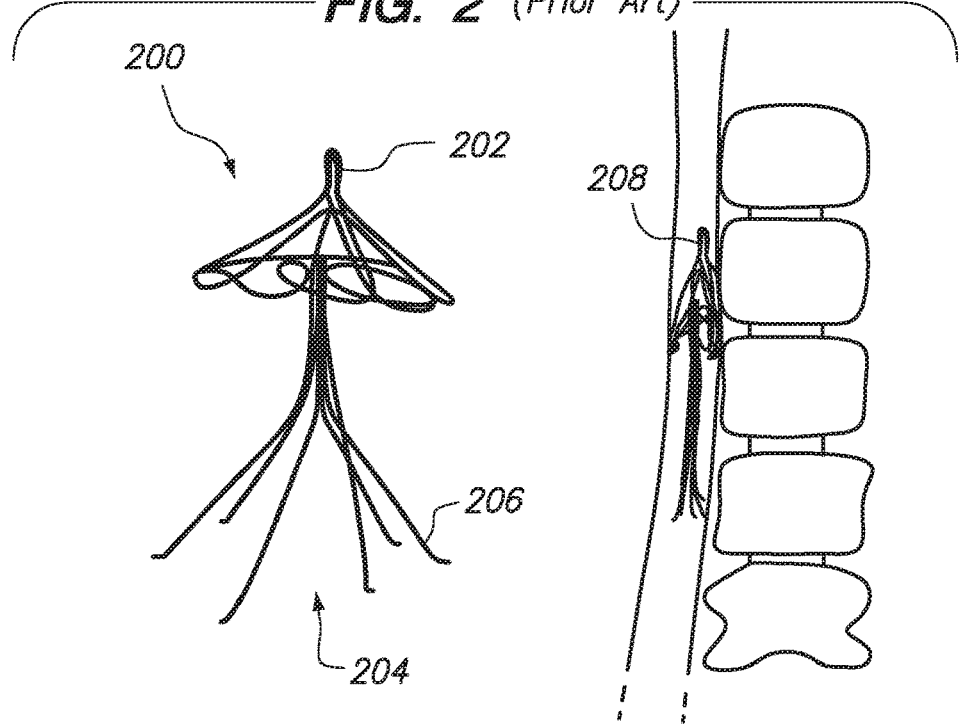
FIG. 2 illustrates an existing inferior vena cava filter and the proximate location of the filter in the upper abdomen.

FIG. 2 illustrates a known inferior vena cava vascular filter that is surgically implanted into the patient's upper abdomen. This inferior vena cava filter (IVC filter) 200 is commonly deployed using a large bore catheter and access to a large bore vein such as the inferior vena cava. The IVC filter 200 has a first end 202 and a second end 204 where the second end comprises a plurality of individual wire components 206. In the proximity diagram of FIG. 2, an IVC filter 200 is shown within the inferior vena cava at location 208 in the upper abdomen of a patient.

Figure 3:
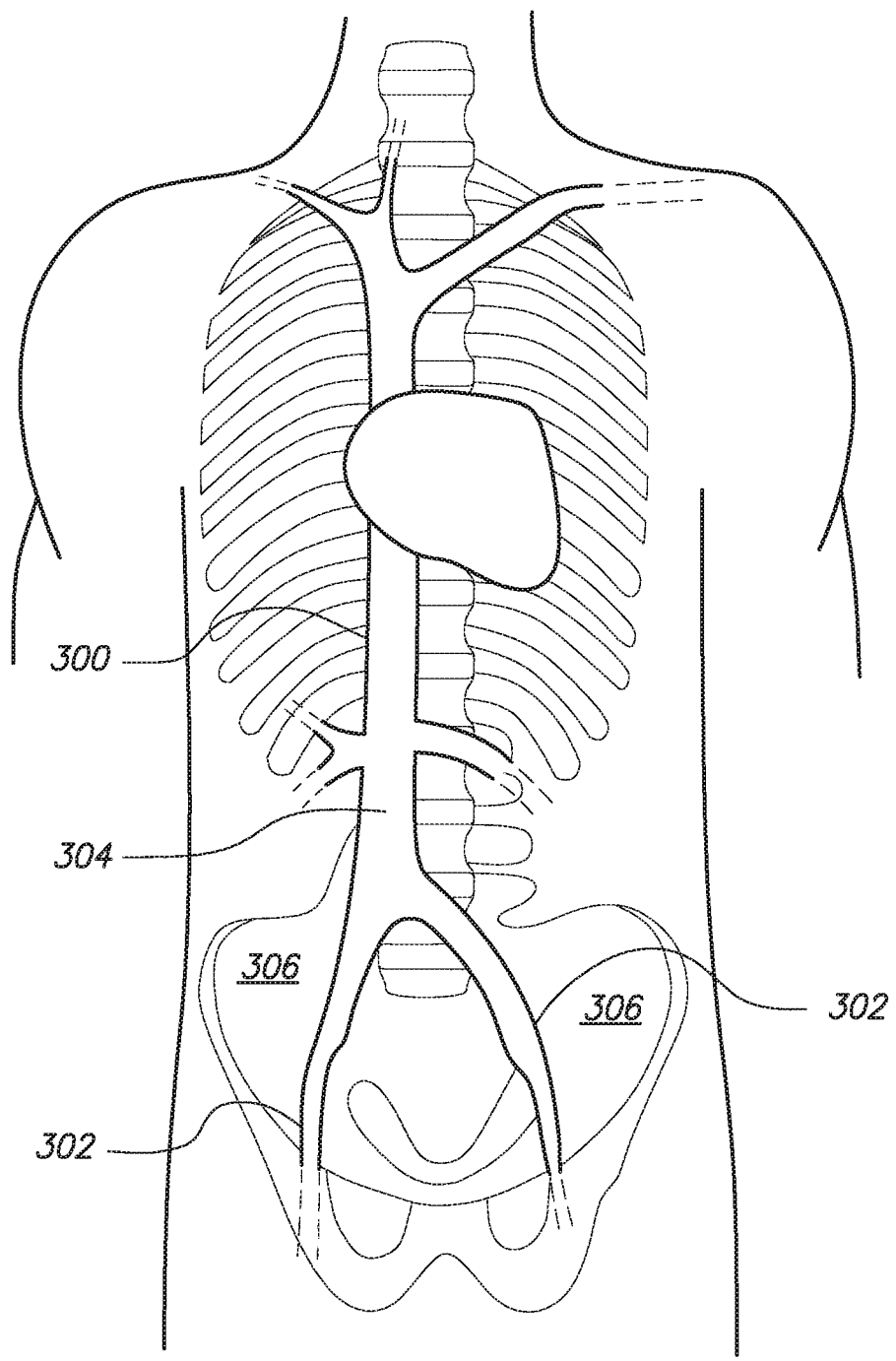
FIG. 3 illustrates the inferior vena cava and the two femoral veins.

FIG. 3 illustrates the inferior vena cava 300 and two common femoral veins 302 branching off the inferior vena cava. In the known use of intravenous filters such as the IVC filter discussed above, it is common to place the IVC filter within the inferior vena cava 300 at location 304 in the upper abdomen.

As stated above, placement of an IVC filter within the inferior vena cava 300 is expensive, requires special surgical procedures, requires imaging from a radiology or cardiology suite to ensure correct placement with the inferior vena cava, and is a substantially difficult and complicated surgery. In addition, known IVC filters must be placed in a large bore vein, and the placement surgery itself poses a significant risk in patients with conditions that prevent proper blood clotting.

The vascular filter in the disclosed embodiments has several advantages over known filters. In contrast to the above, the vascular filter of the disclosed embodiments may be placed within one of the common femoral veins 302. In addition, the vascular filter may be placed at any other location in the body which is suited to capture or retain blood clots to prevent the clots from migrating to more critical areas. The vascular filter may be placed "blind" without imaging guidance from an expensive radiology or cardiology suite. Furthermore, the vascular filter may be placed in the common femoral vein 302 at hip level which is an area routinely used for catheter and other line access.

Use of this common access area is another advantage in that such use of a commonly accessed area tends to reduce complexity and risk during placement as it is a well-known access area.

Though placement at hip level has advantages, placement at hip level may not be ideal in all patients and thus the vascular filter may also be placed in other areas. For example, in one embodiment, the filter may be placed in the groin region 306 of the patient. It is contemplated that the vascular filter may be placed where it is best able to capture a dislodged blood clot and that more than one filter may be placed to ensure that any dislodged blood clots are captured. For example, in one embodiment the vascular filter may be placed in both of the common femoral veins 302 should the patient's medical condition require filtration of both legs. In other embodiments, additional vascular filters may be placed as well.

Placement of the vascular filter begins by accessing a common femoral vein 302. Though the following description describes an embodiment of the present invention where the vascular filter is placed within a common femoral vein 302, the vascular filter may be similarly placed in other veins where dislodged blood clots may be captured as necessary.

Figure 4:
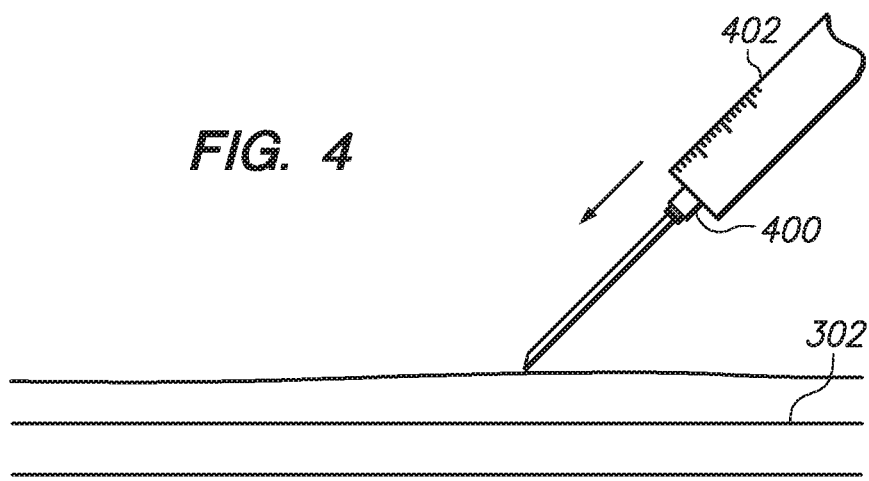
FIG. 4 illustrates a common femoral vein prior to access by a needle and syringe assembly.
Figure 5:
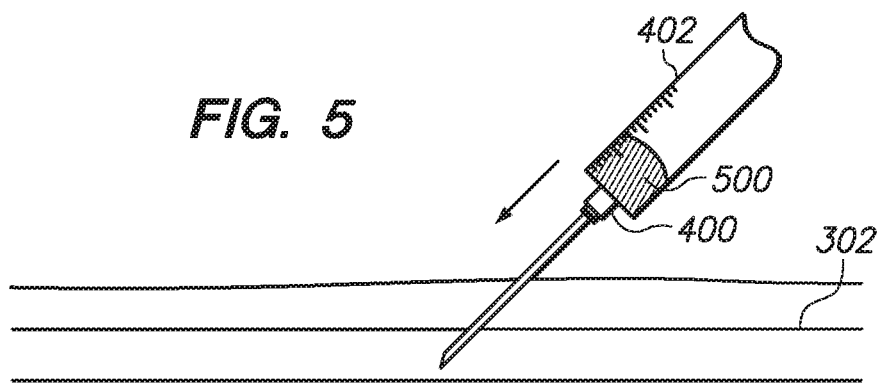
FIG. 5 illustrates actual needle and syringe assembly access into the common femoral vein.

FIGS. 4 and 5 illustrate a common femoral vein 302 accessed by a dispensing needle 400 and syringe 402 assembly. In one or more embodiments, the needle 400 has a first or delivery end through which a vascular filter is implanted in a patient, and a second or coupling end at which a syringe or filter dispenser may be attached. Notably, the coupling end in one or more embodiments may be configured to permit releasable attachment of the needle 400 as described further below.

Generally, proper access to the common femoral vein 302 may be verified by syringe aspiration (drawing blood from the vein into the body of the syringe) and is visually confirmed by blood return 500 into the syringe. In other embodiments, elements other than a syringe may be utilized including, but not limited to a single hollow large bore needle of which the blood can be seen flowing out of without syringe aspiration.

Figure 6:
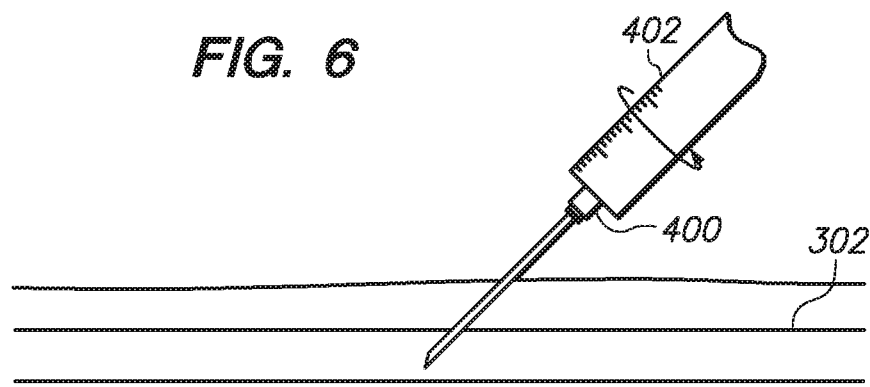
FIG. 6 illustrates removal of the syringe.

As illustrated in FIG. 6, the syringe 402 may be disengaged or removed from the needle 400 without removing the needle from the common femoral vein 302. In one or more embodiments, proper access to the common femoral vein 302 may be confirmed prior to disengaging the syringe 402 by inspecting the syringe for blood return. Such blood return confirms that the needle 400 is within a vein.

It is noted that disengagement or removal of the syringe 402 from the needle 400 may occur in various ways and that the syringe is releasably attached to the needle. For example, the syringe 402 may be fitted with a bayonet type of locking mechanism that retains the needle 400 within the end of the syringe. In addition, any other type of mechanism in addition to or other than a bayonet type locking mechanism may be utilized including but not limited to a manufactured threaded coupling system with "male and female" thread components. The locking mechanism may be any type of configuration that releasably retains the needle in the syringe and because these mechanisms are well known in the art they will not be described in detail so as not to obscure the present invention.

Figure 7:
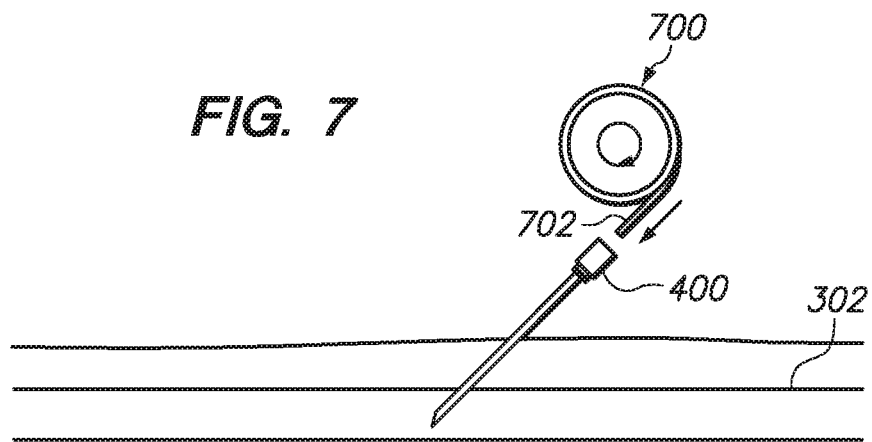
FIG. 7 illustrates attachment of the filter dispenser to the needle.

Attachment of the vascular filter dispenser 700 to the needle 400 is illustrated in FIG. 7. In one embodiment, the vascular filter dispenser 700 is a spool device that is configured to house and dispense filter wire housed within the dispenser. The vascular filter dispenser 700 is fitted with a guide tube 702 that facilitates the deployment of the filter wire from the dispenser through the needle 400 and into the common femoral vein 302. It is contemplated that the end of the guide tube 702 be sized for operative insertion into the inner diameter of the needle 400. The guide tube 702 provides a smooth transition for the filter wire during the deployment process as the wire leaves the filter dispenser 700 and enters the needle 400. In some embodiments, filter means other than a wire may be utilized such as but not limited to monofilament strand or other materials with reformable properties. These structures may be pre-formed or shaped and/or configured at the time of use.

Figure 8:
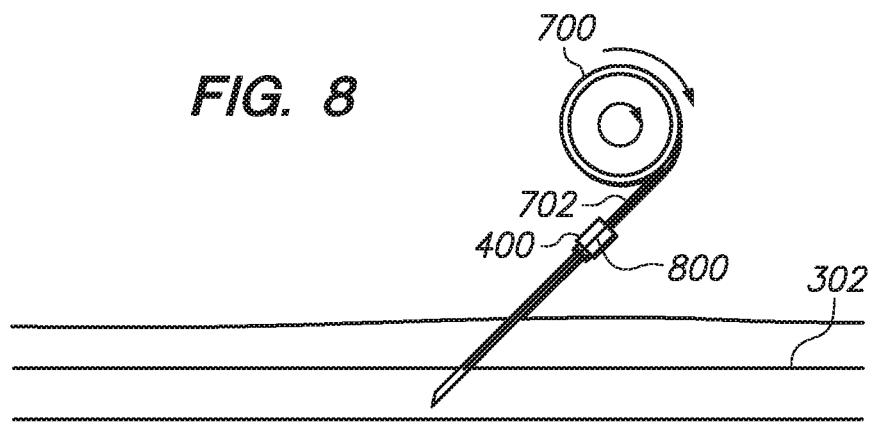
FIGS. 8, 9, 10, and 11 illustrate deployment of the vascular filter, shown with the vascular filter in first, second, third, and fourth positions, respectively.

Reference is now made to FIGS. 8 through 11 individually and in combination for illustrating the deployment of the vascular filter. As shown in FIG. 8, a needle 400 and a vascular filter dispenser 700 are coupled together, and the filter dispenser is actuated such that the filter wire 800 is fed from the dispenser through the needle and into the common femoral vein 302. In one embodiment, the filter dispenser 700 is actuated by a rotational movement of the dispenser so that the filter wire 800 is un-coiled and fed down the guide tube 702 and into the needle 400. It is contemplated that the filter dispenser 700 may comprise a user-rotatable wheel or knob in one or more embodiments. When rotated, the knob un-coils the filter wire 800 and feeds the wire 800 down the guide tube 702. The knob may un-coil the filter wire 800 through physical contact with the filter wire. However, it is contemplated that there may be an attached reel which is actuated by rotational movement of knob. Other embodiments of the filter dispenser 700 are contemplated such as a linear dispenser by which the filter wire is translated down the length of the dispenser and into the needle.

Figure 9:
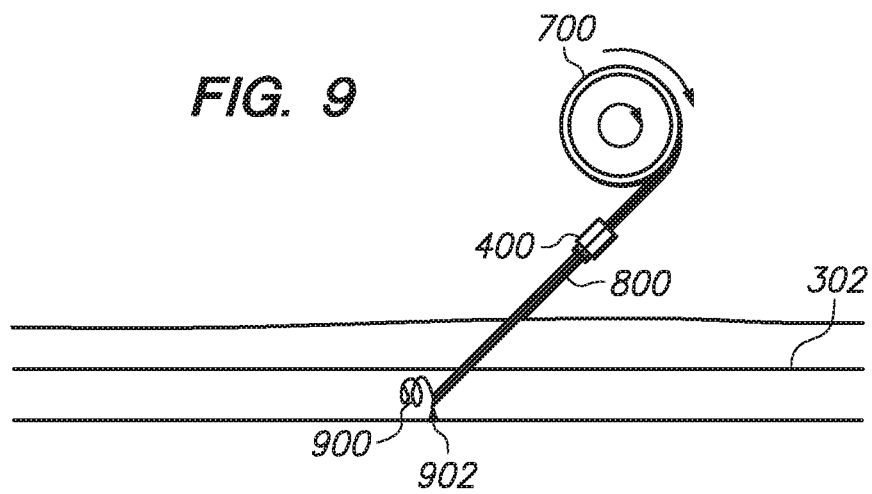

As best illustrated in FIG. 9, as the filter wire 800 traverses down the needle 400 it remains substantially straight. However, when the filter wire 800 exits the end 902 of the needle 400, the filter wire begins to form a coil 900 within the common femoral vein 302. The filter wire coils due to residual stresses of the wire and the preformed shape memory imparted into the wire during the manufacturing process.

In one or more embodiments, the filter wire 800 has a first and a second end and is preferably fabricated from a suitable material such as titanium, Nitinol, or monofilament strand, to name a few. The filter wire 800 may also be fabricated from a polymer as well. The wire may be similar to known wires commonly used in the medical industry and, in one or more embodiments, may range in diameter from 0.015-0.035 of an inch. Additionally, the filter wire 800 may be treated with a compound that prevents clot formation on the wire such as a Heparin anticoagulation coating. The wire may comprise a mesh form or may be constructed of metal, plastic or a combination thereof or any other material. In addition, the filter wire 800 may have a very flexible tip at its first end to reduce the possibility of damaging the inside wall of a vein when the filter wire is implanted.

In one embodiment, an important characteristic of the filter wire 800 is that the wire be preformed to have residual stresses and/or surface tensions such that the wire will automatically coil once advanced beyond the delivery needle end 902. For example, the filter wire may be fabricated so that the surface tension along the length of the wire causes the wire to naturally coil unless otherwise constrained. In this way, the filter wire 800 may be housed or stored in one dispenser configuration and upon proper deployment; the filter wire would coil into a predetermined shape. In another embodiment, the filter wire may be performed to take any various shapes that will achieve the goals set forth herein. For example, the filter wire may be pre-formed to have a vortex shape (coils of increasing/decreasing diameter) once deployed. Other embodiments may provide filter wire that is preformed to have a nesting or tangled web shape.

Figure 10:
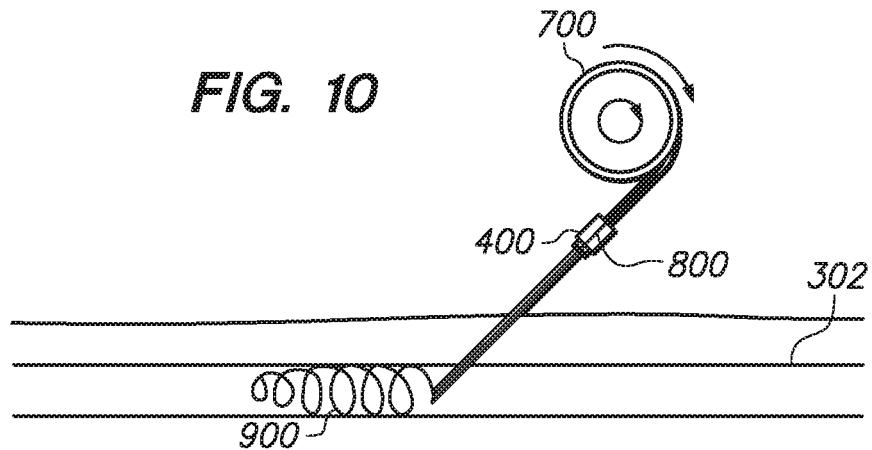
Figure 11:
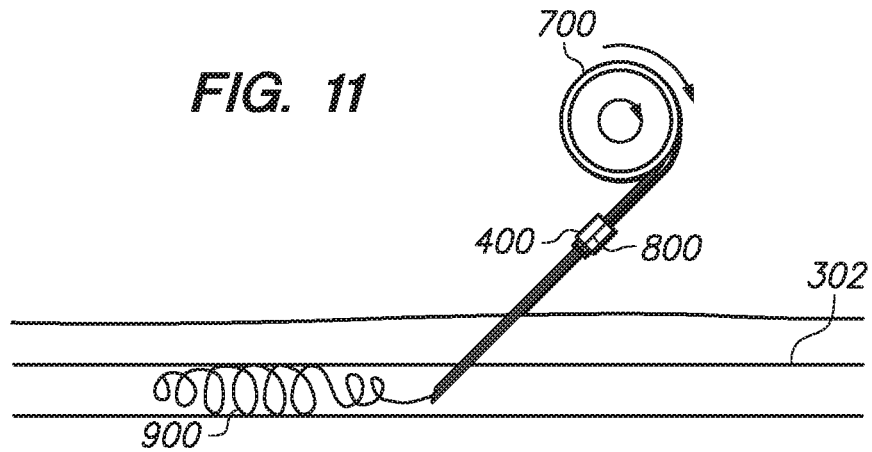

As illustrated in FIGS. 10 and 11, as the filter wire 800 is advanced into the common femoral vein 302, the coil 900 becomes larger and longer such that a substantial coil of wire is formed within the vein. As a result, the coil 900 becomes a partial flow restriction within the common femoral vein 302 capable of capturing and retaining a blood clot therein.

Figure 12:
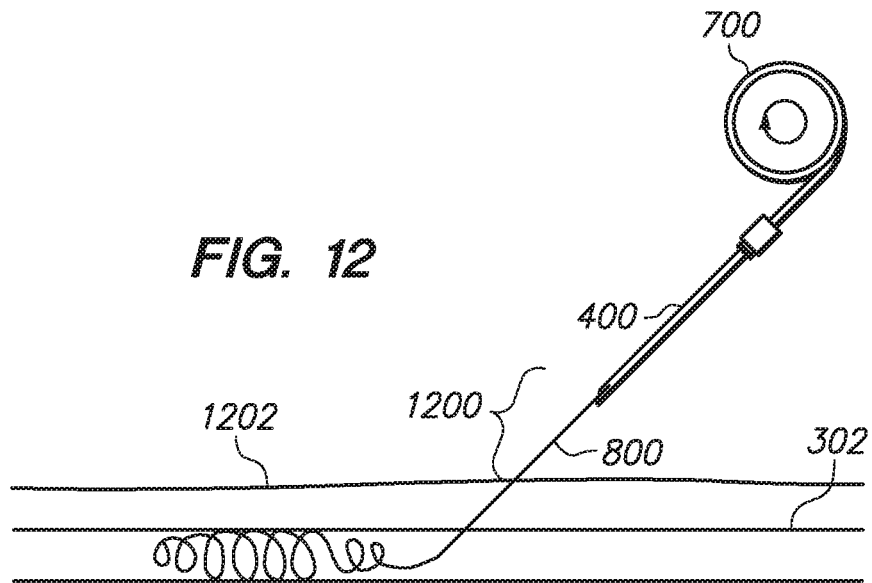
Figure 13:
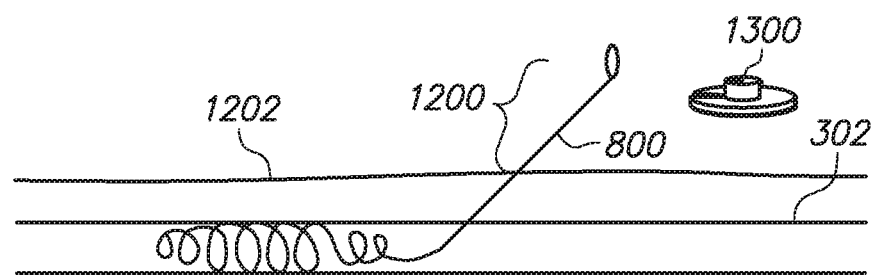
Figure 14:
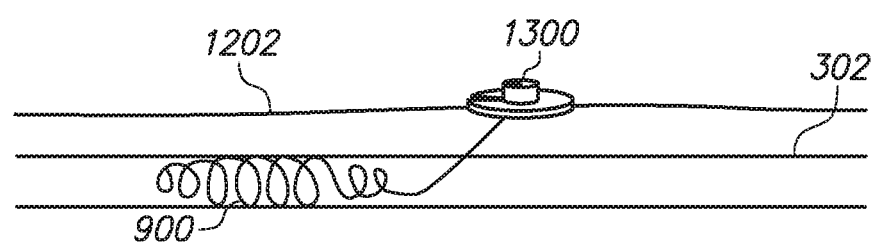
FIG. 14 illustrates retention of the filter wire to the patient's leg.

In FIG. 12, the filter wire 800 has been deployed and the filter dispenser 700 and delivery needle 400 are retracted from the subject's common femoral vein 302. As the dispenser 700 and needle 400 are removed, a portion 1200 of the filter wire 800 may be left protruding from the subject's skin surface 1202 so that it may be secured to a fixation device 1300 (FIG. 13) to prevent the filter wire 800 from moving within the vein. As illustrated in FIGS. 13 and 14, a portion 1200 of the filter wire 800 is intentionally left protruding from the subject's skin surface 1202 so that it may be looped and subsequently attached to a fixation device 1300. The fixation device 1300 is then secured using a medical dressing to the subject's skin 1202 and may cover the filter wire's exit. It is contemplated that types of fixation devices 1300 other than those illustrated in the figures may be used, and that in other embodiments the protruding portion 1200 of the filter wire 800 may be attached in other ways such as by tying or adhering the filter wire to the fixation device.

Figure 15:
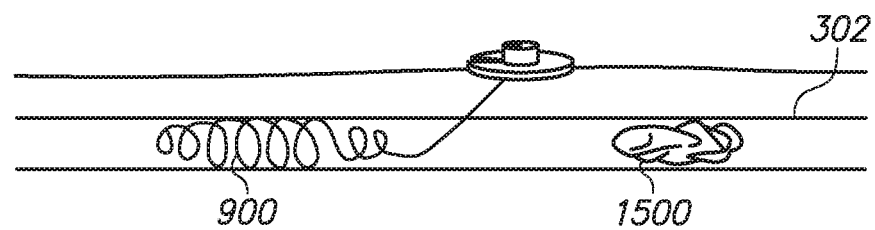
FIG. 15 illustrates a blood clot approaching the deployed vascular filter.
Figure 16:
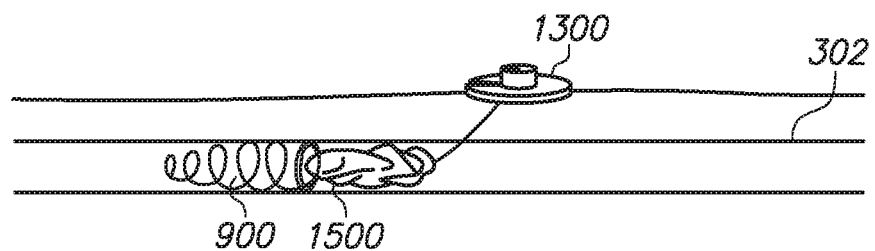
FIG. 16 illustrates the blood clot of FIG. 15 trapped by the vascular filter.

FIGS. 15 and 16 illustrate a blood clot 1500 approaching and being captured by the deployed vascular filter. As the blood clot 1500 migrates down the vein, it will encounter and preferably become trapped by the coil 900 of the vascular filter. As illustrated in FIG. 16, the blood clot 1500 will become lodged or entangled with the vascular filter's coils, and, in this way, the clot is prevented from entering other regions of the subject's circulatory system.

In the event that a blood clot 1500 is captured by the vascular filter, the clot may be removed in one of several ways. First, the entangled blood clot 1500 may be verified using ultrasound or x-ray techniques. If there is a blood clot 1500, then the blood clot may be dissolved using anticoagulation therapy or any other means. If the blood clot 1500 does not dissolve in a timely manner, the attending physician may decide to perform additional procedures such as thrombectomy or thrombolysis to resolve the blood clot. In some cases, permanent placement of a standard IVC filter may be required where the blood clot does not dissolve.

Figure 17:
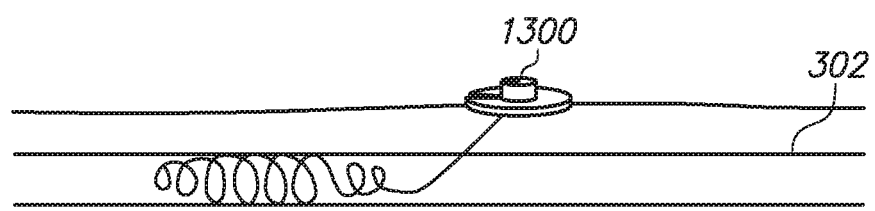
FIGS. 17, 18A, 18B, 18C, and 18D illustrate removal of the vascular filter, shown with the vascular filter in fifth, sixth, seventh, eighth, and ninth positions, respectively.
Figure 18A:
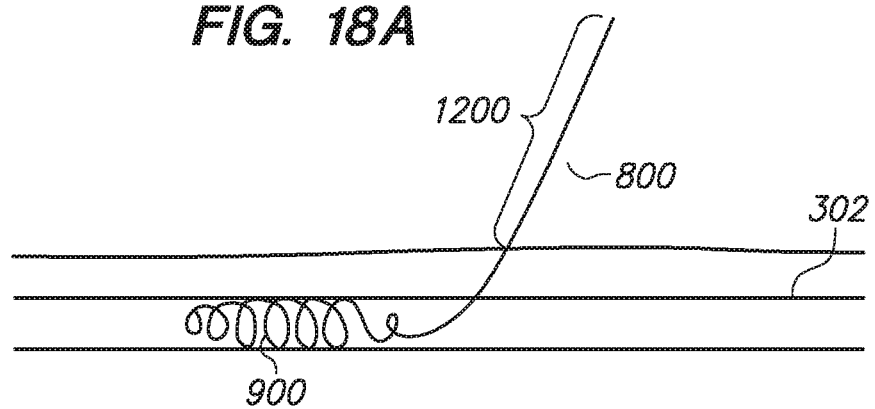
Figure 18B:
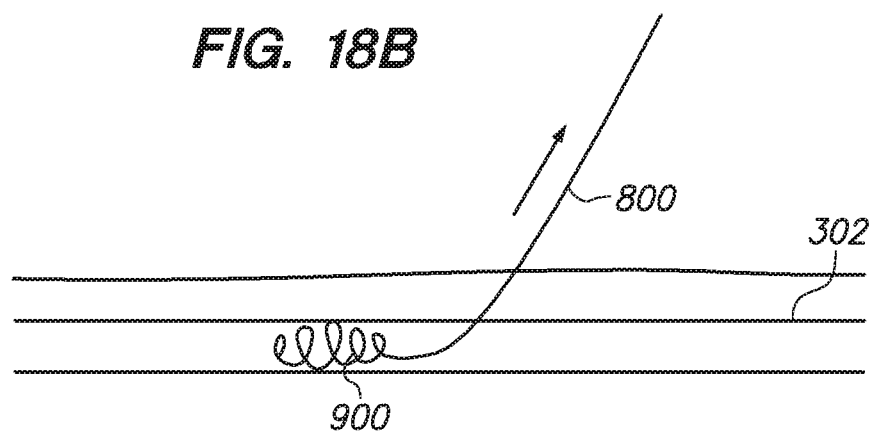
Figure 18C:
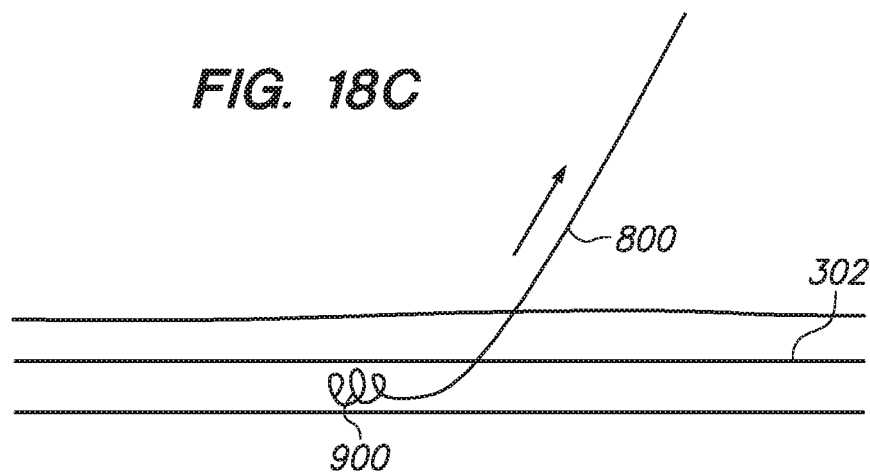
Figure 18D:
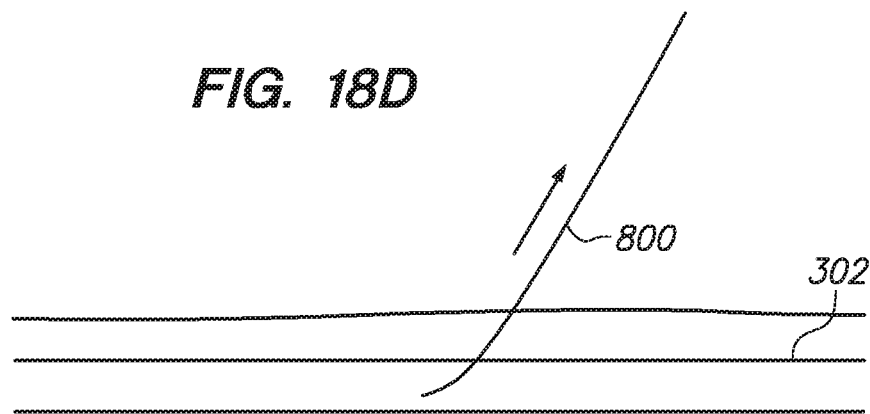
Figure 19:
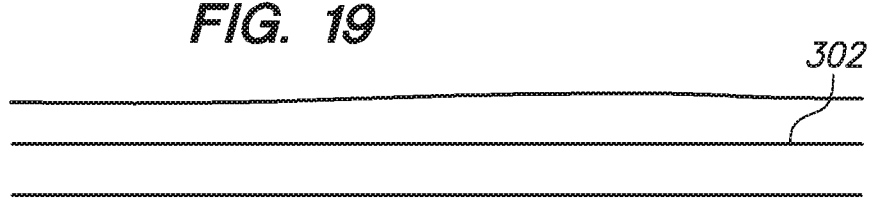
FIG. 19 shows a vein devoid of a vascular filter.

FIGS. 17 through 19 illustrate removal of the vascular filter. In FIG. 17, the fixation device 1300 and associated dressing are removed from the patient's skin surface 1202. Next, the protruding portion 1200 of the filter wire 800 is drawn away from the patient. As the filter wire 800 is drawn out of the patient, the filter coil 900 unwinds and/or unravels as illustrated in FIGS. 18A through 18D. A hydrophilic coating or hydrophilic filter wires 800 may be used, in one or more embodiments, to facilitate removal of the filter coil 900. Once the filter wire 800 is completely extracted from the patient as shown in FIG. 19, the vascular filter has been successfully removed and may be discarded.

The vascular filter disclosed herein has several advantages over known IVC filters. The new vascular filter is inexpensive and easily deployed/removed with minimal intrusion to the patient. In contrast, existing vascular filters require a complex and potentially risky deployment procedure which is very expensive, requires a team of medical professionals and the use of an operating room or cardiology suite.

Additionally, existing vascular filters require an even more complicated and risky procedure for removal.

The new vascular filter is placed without the need for complex fluoroscopic guidance (i.e., the new filter may be placed blindly). For example, unlike existing filters that are placed within the inferior vena cava which requires x-ray fluoroscopic guidance for deployment, the new vascular filter may be placed without using any x-ray or imaging equipment.

The new vascular filter is minimally invasive and can be deployed at the patient's bedside or in an emergency room setting. Correspondingly, removal of the new vascular filter may be performed at a convenient location such as bedside.

The new vascular filter reduces the risk of complications because the filter is placed in a more conducive location within the patient's body. As disclosed herein, the new vascular filter may be placed in the pelvic or groin region of the patient unlike existing IVC filters which are generally placed in the upper abdomen or thoracic region. As a result, the new vascular filer is placed within one or both of the more accessible common femoral veins and is minimally intrusive for the patient. Another desirable aspect of the new vascular filter is a substantial reduction in recovery time for either deployment or removal of the new filter. In contrast, the existing filters require a substantial recovery time for both deployment and removal.

As an improvement to the filter and method of use described above, also disclosed is the filter configured as a route for infusion of fluids, gels, or medications through the filter and into the blood stream. The infused material may medicate the entire body or vascular system, or just the area of the filter. As such treatment can be directed to a very direct and focused area of the body or arterial system. As discussed above, the filter may be used to retain clots and as such, while the clot is retained within the filter, medication may be applied or infused through the filter as disclosed below to target the retained clot. This provides the benefit of concentrating the medication to the clot which is particularly useful for application of clot dissolving medication such as, but not limited to, Tissue Pasminogen Activator (TPA—Alteplase). In addition, it is also contemplated that medication may be infused through the filter as described below to prevent clotting of the blood around or onto the filter, or any other type of build-up of material or growth on the filter. This extends the effective life of the filter within the body and increases the ease of removal.

FIG. 20 illustrates an infusible filter and associated hub assembly. As discussed above, the filter 1600 is located within the vascular system, such as vein 1604 located below the surface of the skin 1608. A hub attachment 1620 connects to the externally located end 1624 of the filter 1600. The base function of the filter 1600 operates as described above and in connection with FIGS. 1-19. In this embodiment the filter 1600 including the externally located end 1624 includes an inner passageway that is configured to conduct medication or other material such as a liquid or gel. The passageway may comprise a lumen.

The filter wire maybe categorized into a perforated section 1630 which is contained within in the vascular system. The filter wire also includes an un-perforated section 1634 that connects the perforated section 1630 at a distal end and to the attachment hub at the proximal end. The perforated section has one or more openings (shown in FIG. 21) through which the medication or other material may exit the filter. The number and shape of the openings may be varied to meet the requirements of the filter, medication, and particular medical application.

The filter sections 1630, 1634 includes a passage between an open end at the hub attachment 1620 and the perforations (not shown in FIG. 20) for the movement of the medication or other material into the filter, through the filter, and out of the perforations. The hub attachment 1620, the structure of which is discussed below in connection with FIG. 21, serves several purposes and functions. The hub attachments provides an access port to the internal passage within the filter sections 1630, 1634 to thereby provide an input port for the medication or other material. The hub attachment 1620 also provides a clamping or compression element to open and close the opening into the internal passage of the filter. This controls the flow of medication or other material into and output of the internal passage. The hub attachment 1620 also provides an attachment point and structure to attach a syringe, drip line, medication storage/dispensing device infusion pump, or any other element configured to deliver medication or other material to the filter.

FIG. 21A illustrates a more detailed view of the infusible filter and hub assembly including a close up of the filter wire with infusing mechanism. This is but one possible configuration of the filter and hub assembly. It is contemplated that in other embodiments other configurations may be realized without departing from the claims that follow. For example, different medical applications may require that the disclosed and claimed device interface with other medical devices and as such modifications may be made to the device shown without departing from the scope of the invention and claims.

As shown generally, the filter includes hub attachment 1620 and the filter wire 1600. A non-perforated section of the filter wire connects the perforated filter section to the hub assemble. The filter may be made from any type material that is configured to perform as described herein.

A fluid chamber 1640 configured to connect to the hub assembly, which in this embodiment is a luer lock 1644. The fluid chamber 1640 contains medication or other material which is provided to the filter 1600 and ultimately to the patient. The fluid chamber may be part of a syringe, drip-line, infusion pump or medication administration device or any other element configured to store and connect to a hub assembly. The fluid chamber 1640 may permanently connect to the filter or may be selectively connectable and removable to apply medication or other material to the filter.

Configured to mate with or connect to the fluid chamber 1640 is a luer lock 1644 having a first end 1648 with an opening configured to mate with the external shape of the fluid chamber 1640, in this embodiment a tapered end. The hub attachment 1620 assembly is an addition to the prior art as it allows wire placement, such as for example, through a needle with the eventual needle removal. Once the entry needle is removed the hub assembly 1620 can be applied to the portion of the filter that is external to the body for infusion.

The luer lock 1644 is generally known in the art and not describe in detail herein. As shown the luer lock 1644 has an internal passageway or lumen from the first end 1648 to a second end 1652. In the second end 1652 is an opening 1656 configured in size and shape to accept a proximal end 1660 of the non-perforated section 1644 filter wire. The opening extends toward the proximal end of the luer lock 1644 to a establish fluid (or there material state) passageway with the fluid chamber 1640. Through this fluid passageway medication or other material may be provided to the filter wire 1600. The medication or other material may be pressurized in the fluid chamber 1640 to establish flow into the lower pressure filter wire. The pressure may be established by a syringe or gravity, or any other force to move the medication or other material from the chamber 1640 to the filter wire.

The luer lock 1644 also includes an outer ring 1664 with internal threaded which rotationally interact with an externally threaded inner frame 1668 of the luer lock. Through rotational movement of the outer ring 1664 relative to the inner frame 1668 the outer ring moves in the linear direction between the proximal end 1648 and the distal end 1652.

The movement of the outer ring 1664 relative to the inner frame 1668 crushes an compression element 1670 that when crushed closes the passage between the chamber 1640 and the internal passageway in the filter 1600. The compression element 1670 may comprise any material capable of performing as described herein. The compression element 1670 is a known structure in the luer lock 1646 and it may also be known to pinch or otherwise close the flow of medication or other material into the filter 1600.

In one configuration the non-perforated section 1634 of the filter in contact with the compression element 1670 may comprise a different material or configuration than the portion of the filter not in contact with the compression element. For example, the non-perforated section 1634 of the filter in contact with the compression element 1670 may be flexible and resilient to return to shape after opening, while the perforated section 1630 may comprise a more stiff material capable of functioning as described above as a filter in a vascular environment.

FIG. 21B illustrates the assembly of FIG. 21A with the compression element compressed to close the inner lumen of the view of the filter. As shown the outer ring 1664 is twisted relative to the inner frame 1668 to compress (shown at element 1671) the compression element 1670, which in turn compresses the inner passageway or lumen to stop the flow of medication or other material.

Figure 22:
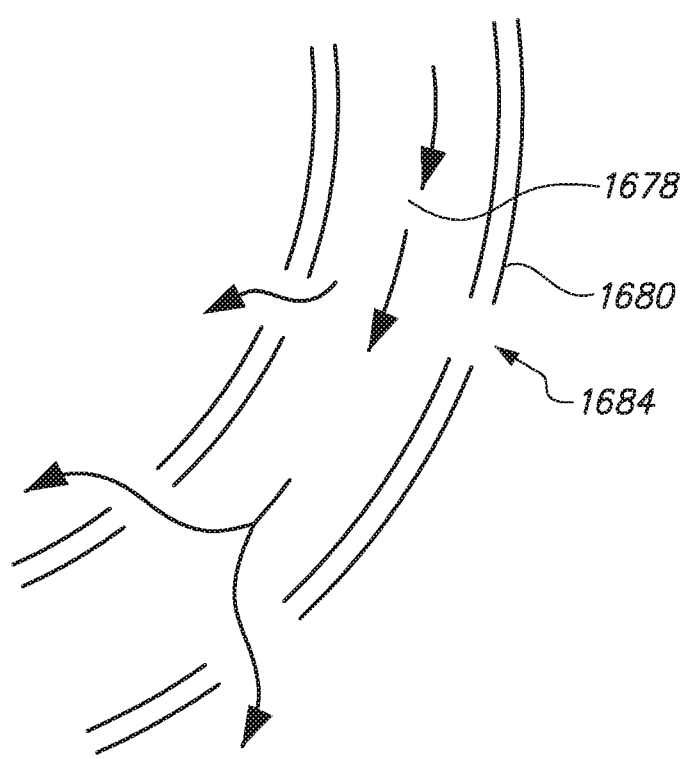
FIG. 22 illustrates a close up view of the perforated section of filter wire with medication outflow holes.

Also shown in FIG. 21A is a close up view 1631 of the perforated section 1630 of the filter. Each of the dots in the coiled filter wire comprise opening or holes through which the medication or other material may pass into the blood steam FIG. 22 illustrates a more detailed version of the filter. As shown the perforated section 1630 of the filter includes an outer wall 1680 which forms an inner passage 1678 or lumen through which medication or other material may flow or be placed. Perforating through the wall 1680 are openings 1684 which provide passages for the medication or other material to exit the inner passageway 1678 or lumen and enter the bloodstream. The openings 1684, which may referred to herein as infusion pores or diffusion pores, may be of any various size and shape and such size and shape may depend on the medication or other material, dosing requirements, patient condition or numerous other factors.

This current improvement allows the place filter to be a route of infusion for fluids and/or medication. The enhanced filter with infusion capabilities can therefore aid in patient care as an extra source of venous access, provides an additional means to protect the filter itself from developing blood clots and potentially will provide a means of breaking up or dissolving the trapped clot via infusion of clot dissolving medications including but not limited to Tissue Plasminoge Activater (TPA) and any other medication now existing or develop in the future.

In summary, once the filter has been placed medication can be infused directly into the blood stream via the inner lumen and multiple infusion pores (openings) located on the intravenous portion of the filter wire. In order to channel fluid through the inner lumen of the filter coil a custom coupling apparatus is provided to attach to a syringe or other device configured to present the medication into the inner passage of the filter wire. The coupler, such as hub assembly, allows for the filter wire with the open inner lumen to be put into fluid communication with a standard IV drip system or other medication administration mechanism via a luer lock connection (hub assembly). Within the coupler is a compression seal (4). When the two coupler bodies are threaded together the compression seal is deformed thus creating a fluid tight seal around the filter wire. Once a seal is made the coupler can be connected to an IV line allowing fluid to pass through the filter wire and infuse into the patient's blood stream.

It is further contemplated that various coatings can be added to the surface of the filter to enhance its biocompatibility or prevent/inhibit growth or development of unwanted surface tissue by the body on the filter. An example is an antithrombogenic antiplatelet coating or material to prevent development thrombi in vitro. This may further prevent or reduce development of clots or scar tissue development on the vascular filter.

Figure 23:
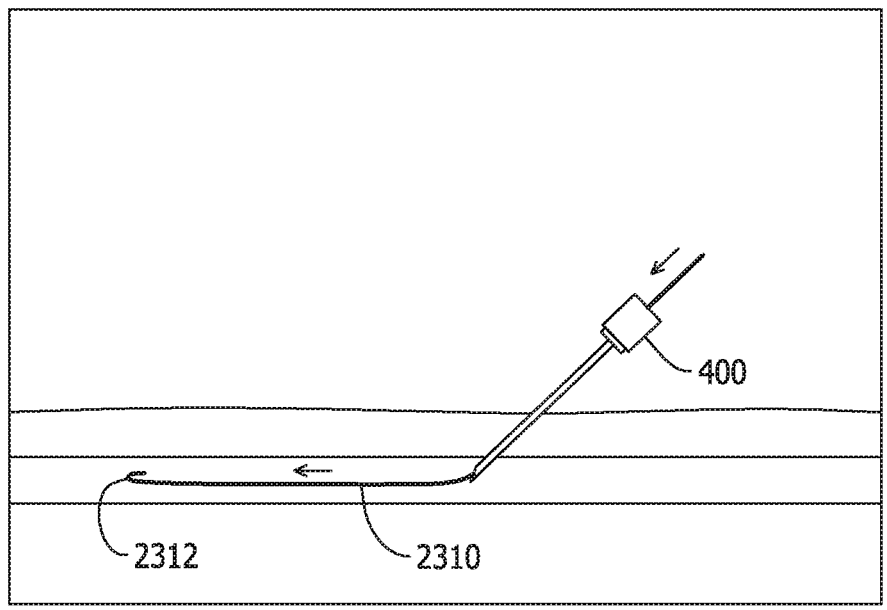
FIGS. 23 and 24 illustrate the deployment of a guidewire into the common femoral vein shown with the guide wire in first and second positions, respectively.
Figure 24:
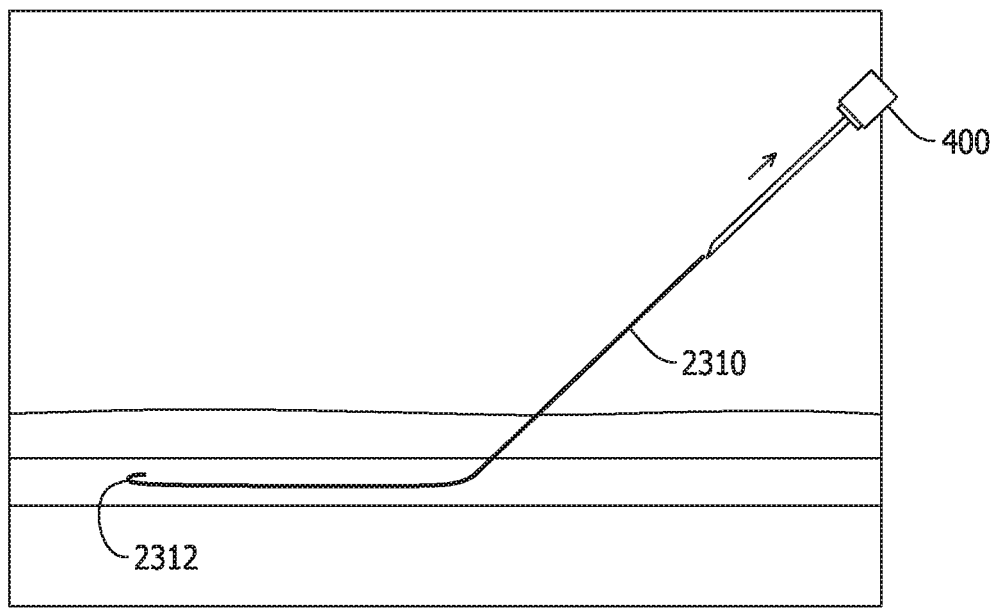

The above-described vascular filters may also be inserted and removed by other methods. In FIG. 23, the needle 400 is inserted into a patient's vein, such as the common femoral vein. A guidewire 2310 is inserted through the needle 400 into the vein. The guidewire 2310 may have a curved tip 2312, such as a u-shaped or a j-shaped tip to facilitate navigation of the guidewire 2310 through the vein and to prevent catching of the guidewire on the vein. The guidewire 2310 may be stored on a reel or other storage device, or inserted as a length of wire. When the guidewire 2310 is deployed in the vein, the needle 400 may be removed as shown in FIG. 24.

Figure 25:
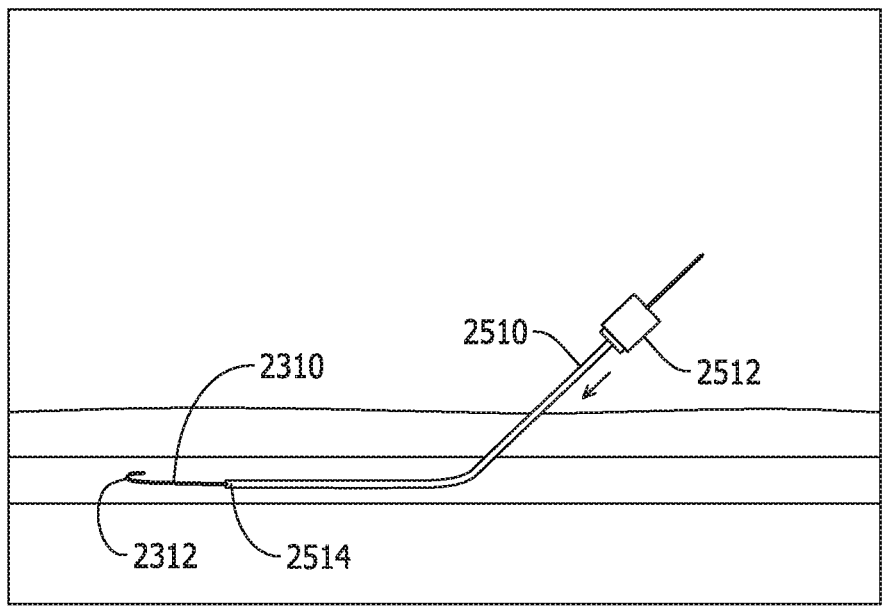
FIG. 25 illustrates the deployment of a catheter along the guidewire.
Figure 26:
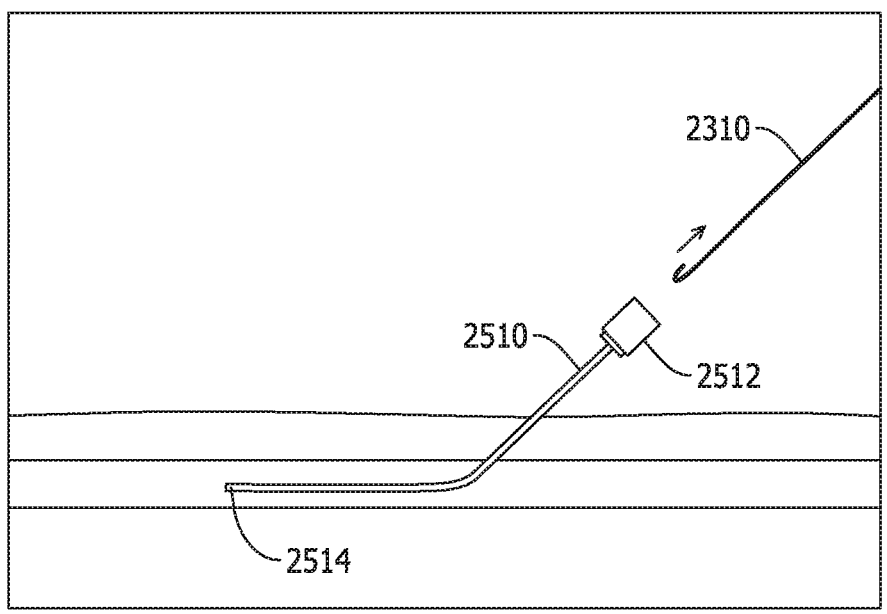
FIG. 26 illustrates the removal of the guidewire.

In addition and in reference to FIG. 25, the guidewire may also be used to establish a sheath or catheter 2510 in a patient. As shown, a sheath or catheter 2510 is utilized to deploy the vascular filter, as will be described in more detail below. The catheter 2510 has a proximal end 2512 and a distal end 2514. A proximal end of the guidewire 2310 outside of the patient is inserted into the distal end 2514 of the catheter 2510, and the catheter is guided over the guidewire 2310 to be inserted into the patient. In this manner, the catheter 2510 is inserted into the patient's vein at a predetermined location along the guidewire 2310. The guidewire 2310 acts as a guide for the catheter. Once the catheter 2510 is properly placed within the vein, the guidewire 2310 is removed by pulling the guidewire 2310 out from the proximal end 2512 of the catheter 2510 as shown in FIG. 26. It is also contemplated that the guidewire 2510 may be left in place to facilitate filter removal, or for other medical procedures.

Figure 27:
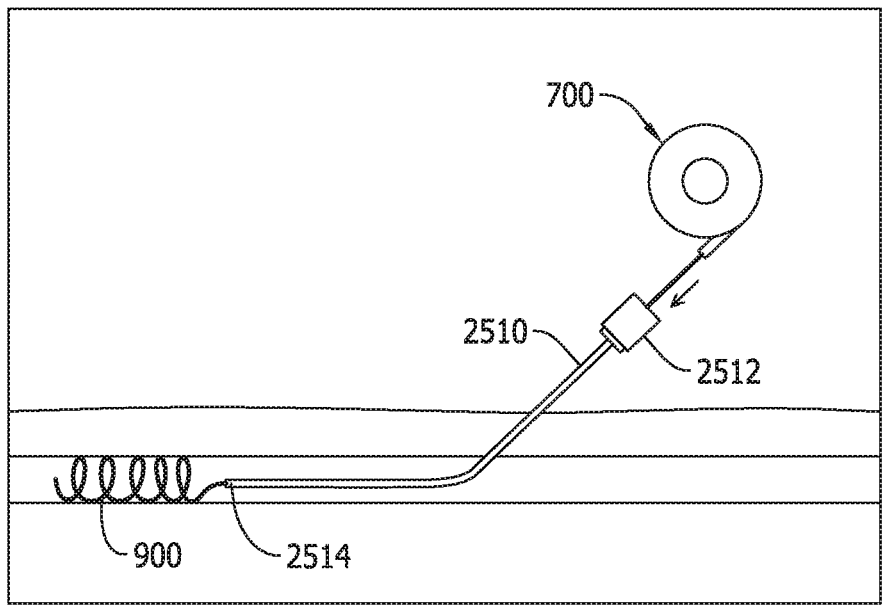
FIG. 27 illustrates the deployment of the vascular filter.

With the catheter 2510 in place, the filter may be inserted in a manner similar as explained with reference to FIGS. 7-11 above. That is, as shown in FIG. 27, a filter dispenser 700 may connect with and insert a distal end of the filter 900 into the proximal end 2512 of the catheter 2510. When the filter 900 exits the distal end 2514 of the catheter 2510, residual stresses in the filter 900 cause the filter wire to coil and form the filter within the patient's vein. In other embodiments deployment in a manner other than coiling may occur.

Figure 28:
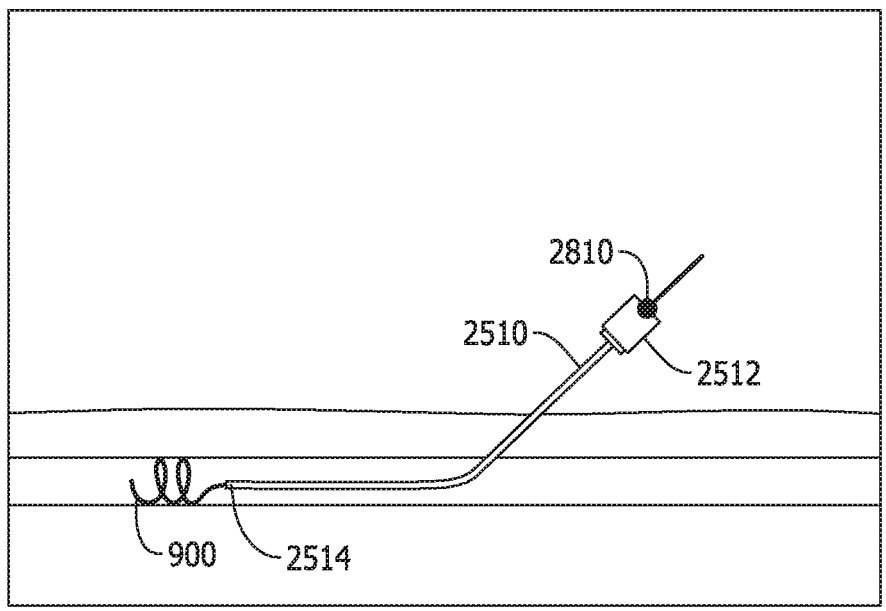
FIG. 28 illustrates the retention of the filter wire in the patient's leg.

In FIG. 28, the proximal end of the catheter 2510 (or sheath) is configured with a valve or seal on or in the exposed end that allows the filter wire (or guide wire) to be placed and advanced/withdrawn without allowing air into the catheter or blood from escaping from the catheter. In this configuration a "plug" may be mainly used to prevent the wire from advancing further into the vein. This plug may be referred to as a "wire fixation clamp or plug". In another embodiment the catheter 2510 is plugged by a fixation plug 2810 or any other device or element such as tape, adhesive, ring/loop or the like. The fixation plug 2810 holds the filter 900 in position with respect to the inserted catheter 2510 and may prevent infection while the filter 900 is in place. The catheter 2510 may be plugged with the fixation plug 2810 or other element to prevent blood flow from the catheter.

Figure 29:
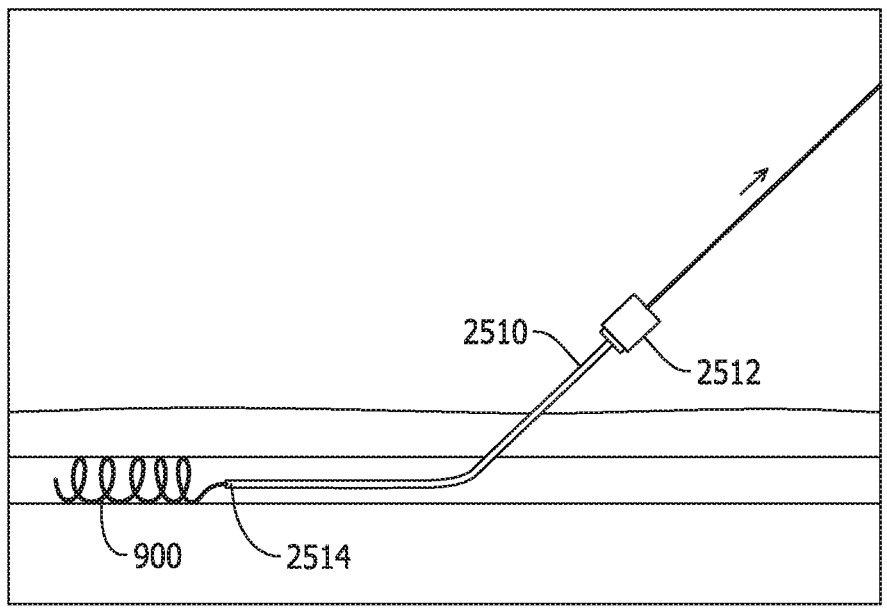
FIG. 29 illustrates the removal of the vascular filter.
Figure 30:
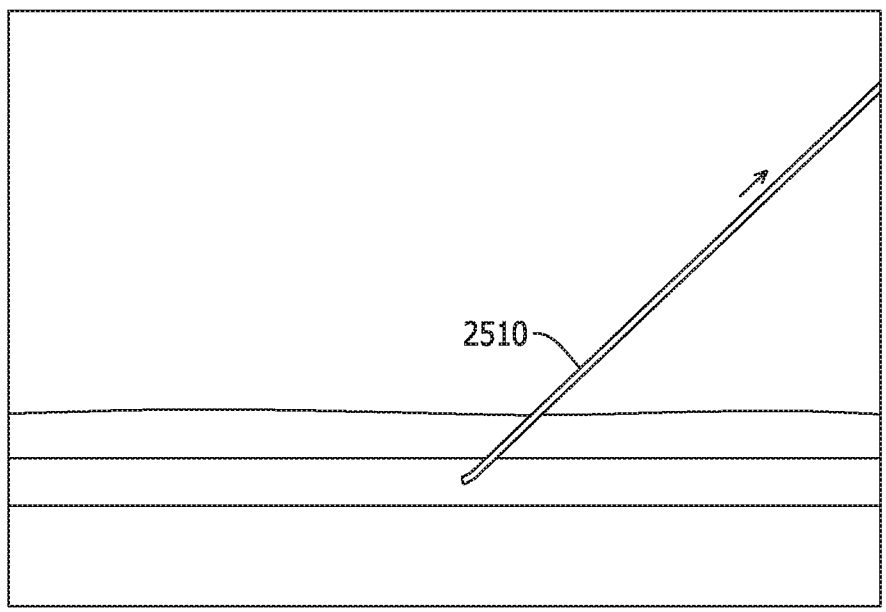
FIG. 30 illustrates the removal of the catheter.

Removal of the filter is shown in FIGS. 29 and 30. Here, the filter 900 is removed by pulling the filter 900 through the catheter 2510 and out of the proximal end 2512 of the catheter. Once the filter 900 is removed, the catheter 2510 is then removed. In this embodiment, the filter 900 may be safely and easily removed by way of the catheter 2510 inserted in the patient. This is due to the pulling force on the filter 900 to be substantially parallel to the vein with the filter is removed through the catheter 2510. The catheter 2510 also protects the skin and vein by providing a protective wall between the filter 900 and the skin and vein. It is contemplated that this system may be used with any type filter such as a filter having an interior passage and outlets for medication disbursement. The filter 900 may also be of any shape and having one or more barbs or rough surfaces to catch the edge of the vein. The filter 900 material may also be smooth to prevent adhesion to the veins.

Figure 31:
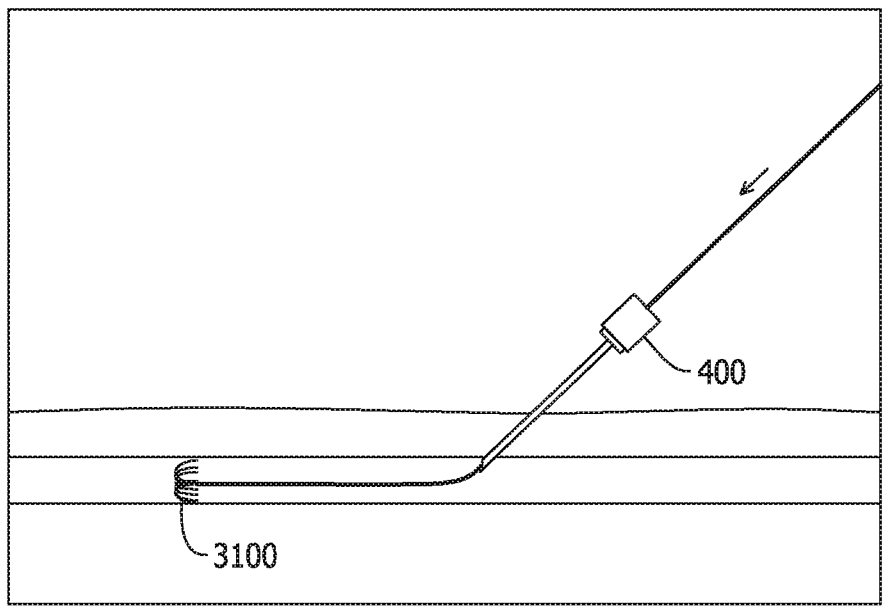
FIG. 31 illustrates the deployment of a vascular filter according to a further exemplary embodiment.
Figure 32:
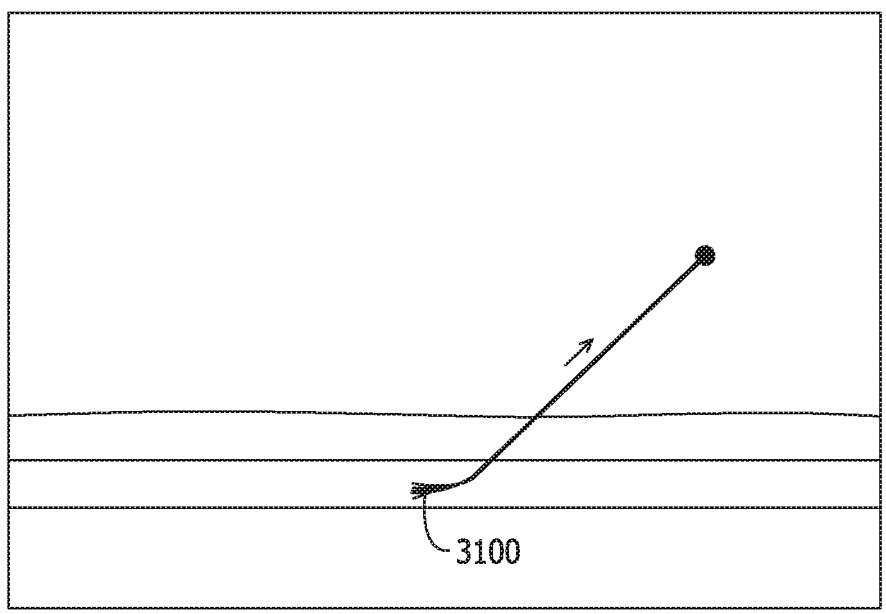
FIGS. 32 and 33 illustrate the removal of the vascular filter shown in FIG. 31.
Figure 33:
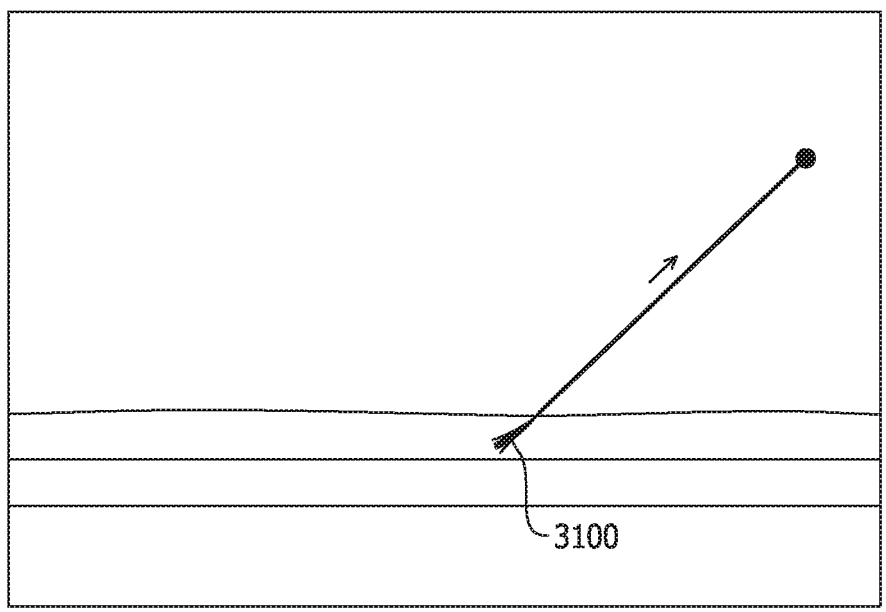

Further modifications may be made within the scope of the invention. For example, as shown in FIG. 31, the filter may be configured to have an "umbrella" end 3100. That is, the end of the filter may be split into several different threads. The filter may deploy from the needle or catheter. The residual stresses within the threads of the umbrella end expand the threads into the umbrella shape 3100 once deployed from the needle 400 (a catheter such as catheter 2510 may also be used). The threads of the umbrella filter 3100 are formed to be flexible such that when the filter is removed, as shown in FIG. 32, the threads flex back and allow easy removal from the vein. It also contemplated that for removal, a flexible sheath may be inserted through a placement needle until the sheath contacts the umbrella portion of the filter causing the threads of the umbrella to collapse backwards and into the sheath for removal from the vessel. Although discussed for use in vein, it is contemplated that the filters may be used in any type or location of blood vessel.

Figure 34A:
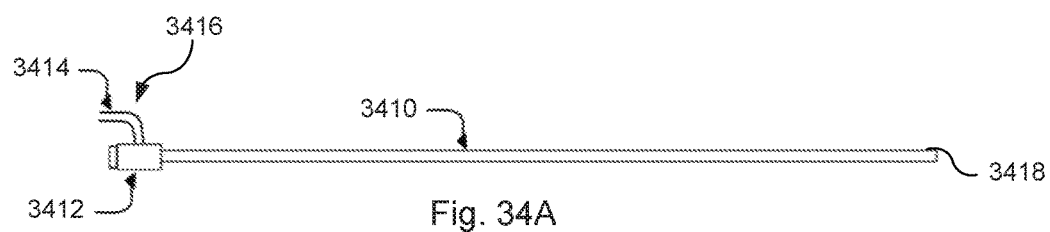
FIG. 34A, FIG. 34B, and FIG. 34C illustrate an exemplary catheter, an exemplary wire, and both the catheter and the wire, respectively, for a thrombectomy.
Figure 34B:
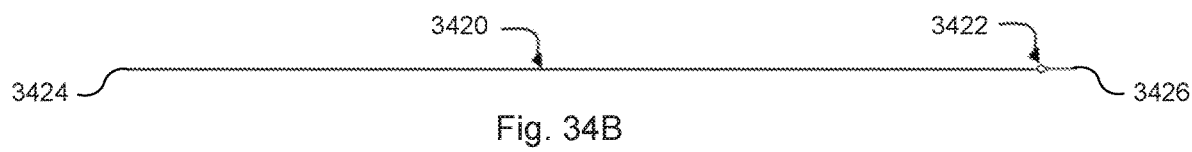
Figure 34C:
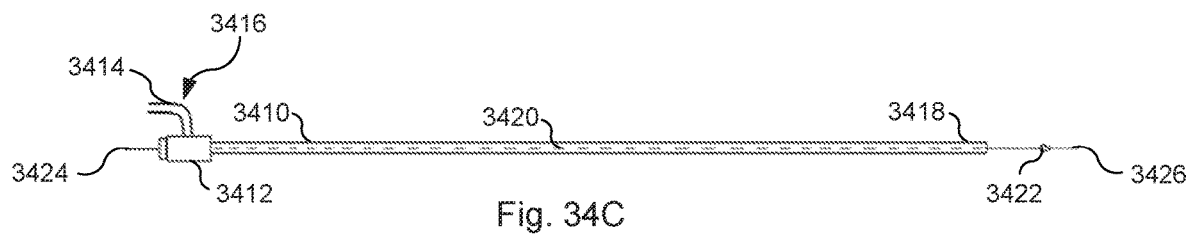

In an exemplary embodiment, the above-described filter may be incorporated into a wire to perform a thrombectomy, as will be explained herein. FIG. 34A, FIG. 34B, and FIG. 34C illustrate an exemplary catheter and wire for a thrombectomy. In FIG. 34A, a thrombectomy catheter 3410 is provided that has a Luer lock hub 3412 at a proximeal end thereof. The Luer lock hub 3412 comprises a side passage 3414 which connects with an aspiration device to provide suction through the catheter 3410 for clot removal.

An exemplary thrombectomy wire 3420 is shown in FIG. 34B. The thrombectomy wire 3420 comprises a bead like element 3422 located near the distal end of the wire 3420. In FIG. 34C, the assembly of the thrombectomy wire 3420 within the thrombectomy catheter 100 is shown. A proximal end 3424 of the wire 3420 extends beyond the proximal end 3416 of the catheter 3420 so that a medical professional can manipulate the wire 3420. The distal end 3426 of the wire 3420 including the element 3422 projects beyond the distal end 3418 of the thrombectomy catheter 3410.

FIG. 35A, FIG. 35B, FIG. 35C, FIG. 35D, and FIG. 35E illustrate operation of an exemplary catheter and wire for a thrombectomy. In FIG. 35A, the catheter 3410 and wire 3420 are shown in the assembled state. Though not shown, the catheter 3410 and wire 3420 are deployed within a vein such that the distal ends 3418, 3426 of the catheter 3410 and wire 3420 are positioned adjacent to a clot 3500, while the proximal ends 3416, 3424 of the catheter 3410 and wire 3420 are positioned outside of the patient's body. As shown by the arrow 3520, suction is applied to the side passage 3414 to try to remove the clot 3500.

In FIG. 35B, the clot 500 is shown to create an occlusion of the distal end 3418 of the catheter 3410. When this occurs, the beaded element 3422 of the wire 3420 is used to pull the clot 3500 into the catheter 3410 to be removed through the side passage 3414. As shown in FIG. 35C, the element 3422 is brought to engage the clot 3500 by manipulating the proximal end 3424 of the wire 3420 as shown by arrow 3530. In FIG. 35D, it is shown that the element 3422 brings the majority of the clot 3500 within the catheter 3410 for removal through the passage 3414. However, in some instances, pieces 3510 of the clot 3500 may be dislodged. Ideally, as shown in FIG. 35E, the remainder of these pieces are removed through the catheter 3510 once the beaded element 3422 is pushed back out of the distal end 3418 of the catheter 3410.

In many circumstances, however, the dislodged portions of the clot may break away and enter the bloodstream. This necessitated the use of filters placed in a procedure prior to the thrombectomy as discussed above. According to the embodiments described herein, a filter is incorporated into the system that allows the filtering of the thrombectomy to be done integrally with the thrombectomy procedure.

Figure 36A:
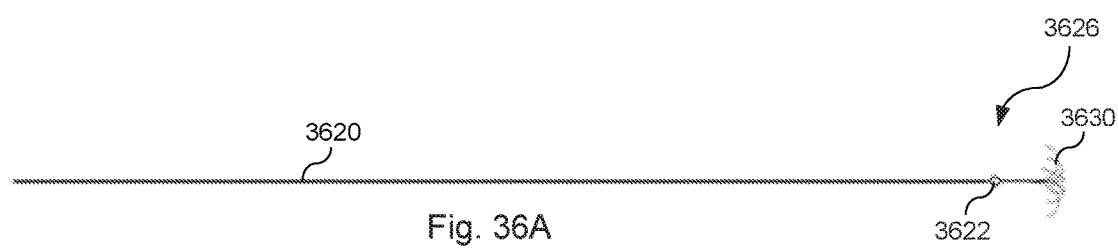
Figure 36B:
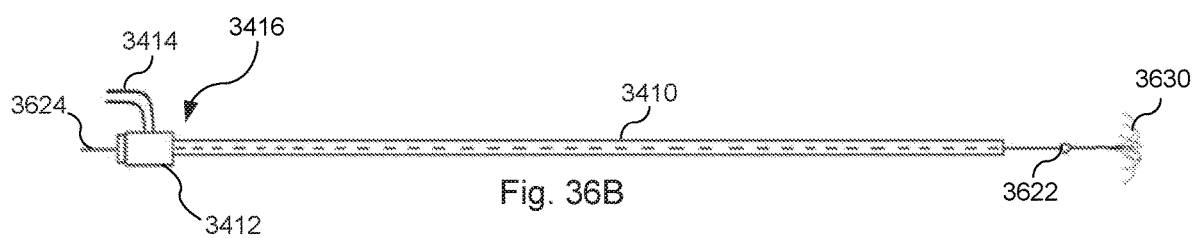

FIG. 36A and FIG. 36B illustrate a thrombectomy filter design, according to an exemplary embodiment. As shown in FIG. 36A, a thrombectomy wire 3620 comprises a beaded element 3622 toward a distal end 3626 thereof. At the distal end 3626, the wire 3620 comprises a filter portion 3630. In this embodiment, the filter portion 3630 is an umbrella shaped filter.

Figure 37:
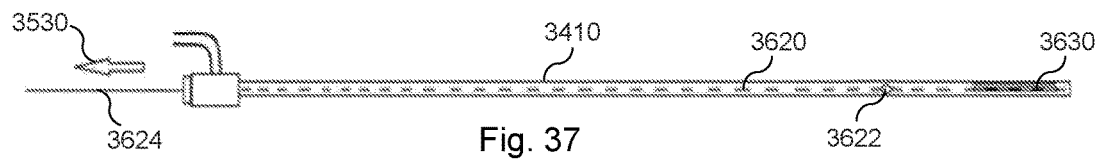
FIG. 37 illustrates a retracted filter portion of a thrombectomy filter design, according to an exemplary embodiment.

The filter portion 3630 is similar to the filters already described herein in that it includes residual stresses such that it can be deployed through the catheter 3410 and deploy into its preconfigured shape upon exiting the catheter 3410. Thus, the thrombectomy wire 3610 may be used with, for example, the thrombectomy catheter 3410 described above. FIG. 37 illustrates a retracted filter portion of a thrombectomy filter design, according to an exemplary embodiment. Here, the filter 3630 is shown retracted within the catheter 3410 as the proximal end 3624 of the wire 3620 is removed as shown by arrow 3530. In this manner, the filter is deployable and removable for the thrombectomy without the need for an extra pre- or post-procedure.

Figure 38:
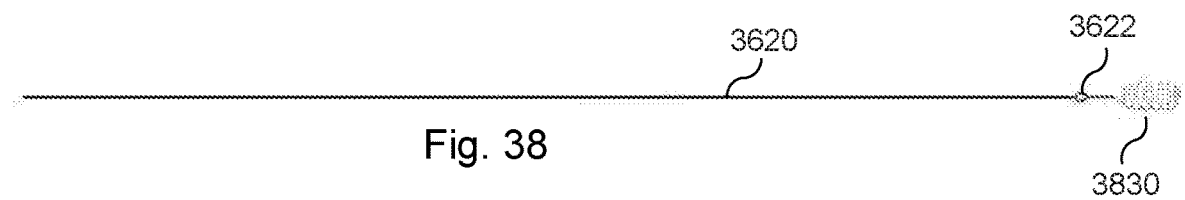
FIG. 38 illustrates a thrombectomy filter design, according to an exemplary embodiment.

FIG. 38 illustrates a thrombectomy filter design, according to an exemplary embodiment. The design of the filter is not limited to the umbrella shape. As shown in FIG. 38, the design may include a coiled or helix shape 3830. Other shapes may also be used such as a vortex shape, a nested shape, and a tangled web shape, or any other shape. The filter may oppose or not oppose the inner vessel wall.

Figure 39:
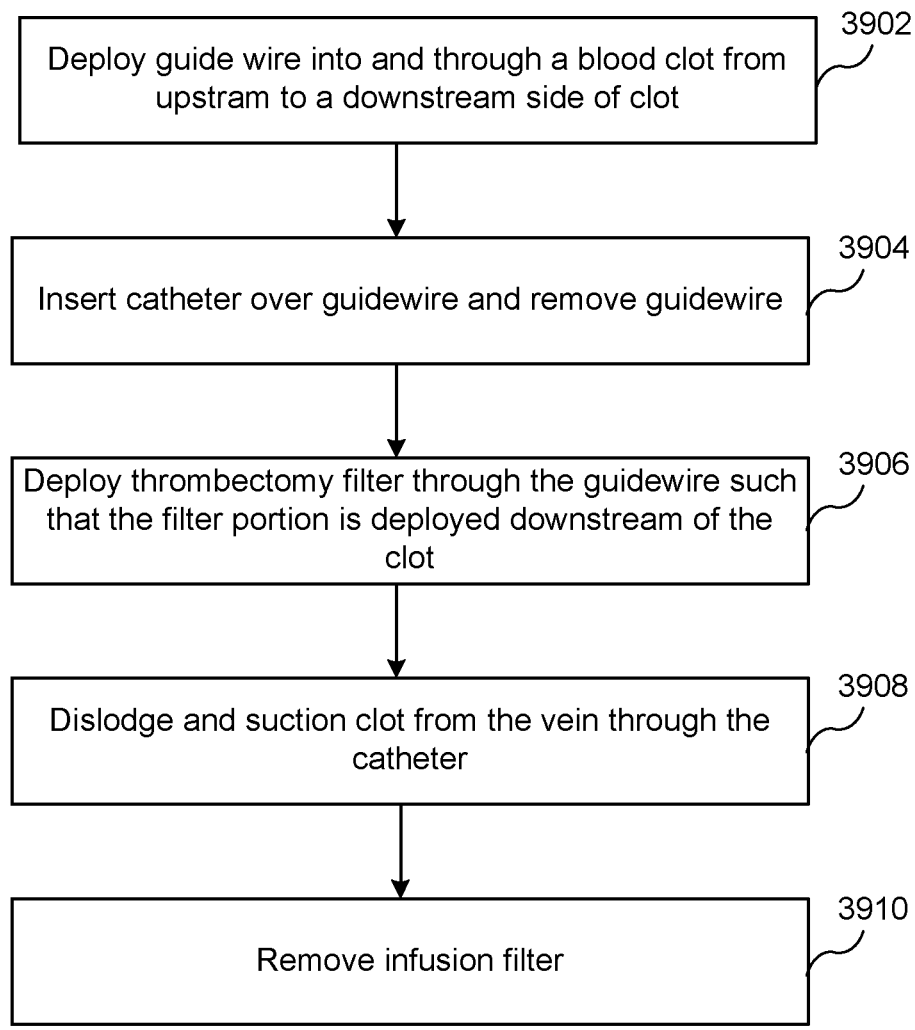
FIG. 39 shows a method for performing a thrombectomy, according to an exemplary embodiment.

FIG. 39 shows a method for performing a thrombectomy, according to an exemplary embodiment. In step 3902, a medical professional deploys a guide wire into and through a blood clot of a patient. For example, a patient may have a blood clot in an upper leg that extends in and through a vein in the upper leg. The guide wire is inserted into the vein upstream from the clot and is directed completely through the clot until a distal end of the guidewire reaches a downstream side of the clot. Once the guidewire is adequately positioned, a catheter is inserted over the guidewire, as described in step 3904. With catheter in position, the guide wire may then be removed.

In step 3906, a thrombectomy filter, such as the one described above, is deployed through the catheter. The thrombectomy filter is positioned so that the filter portion of the thrombectomy filter is deployed downstream in the blood vessel from the clot. When the thrombectomy filter is in place, the medical professional may perform the thrombectomy by dislodging and suctioning the clot from the vessel as shown in step 3908 and as described above.

While the thrombectomy is performed, the filter at the distal end of the thrombectomy filter catches any clot or portion thereof that may become dislodged into the blood stream. Thus, any clot that might break away is filtered and prevented from traveling to other areas of the body where it might cause significant injury or death, such as via a pulmonary embolism. Pieces of the clot caught in the filter may be gradually dissolved via medication dispensed through the catheter after the thrombectomy, or may be suctioned through the catheter when the filter portion is pulled towards the catheter.

In step 3910, the infusion filter may be removed once the treatment is complete. The infusion filter is removed similar to the removal of the filters described above. The filter portion of the infusion filter is designed with pitch angles and materials such that the filter can be pulled back out through the incision.

The thrombectomy filter and method for performing a thrombectomy described above have a number of advantages. First, as compared to prior systems where a filter is deployed and removed by separate procedures, usually by accessing the jugular vein and guiding the filter through the body to be deployed on the downstream side of the clot in the interior vena cava, the present embodiments allow the filter to be easily placed from an access point upstream from the clot. The safety is also increased due to effective filtering of the vein downstream from the clot during the thrombectomy. When the clot is dislodged during the procedure, any large pieces of the clot are filtered and dissolved or removed rather than entering the bloodstream and possibly resulting in a pulmonary embolism or the like. Finally, when the treatment is complete, the filter may be immediately removed without a separate complicated procedure to retrieve the filter.

While various embodiments of the invention have been described, it will be apparent to those of ordinary skill in the art that many more embodiments and implementations are possible that are within the scope of this invention. In addition, the various features, elements, and embodiments described herein may be claimed or combined in any configuration or arrangement.

What is claimed is:

1. A method of performing a venous thrombectomy comprising:
    deploying a guidewire within a blood vessel from an upstream side of a blood clot so that a distal end of the guidewire reaches a downstream side of the blood clot;
    inserting a thrombectomy catheter over the guidewire, the thrombectomy catheter comprising a proximal end and a distal end, the proximal end comprising a leur lock with a side passage;
    removing the guidewire while the catheter is in place;
    deploying a thrombectomy filter wire through the catheter, the thrombectomy filter wire comprising:
        a length of wire having a proximal end and a distal end, the length of wire being configured to deploy through the thrombectomy catheter, the proximal end being configured to manipulate the length of wire when the length of wire is deployed; and
        a filter portion disposed on the distal end of the length of wire, the filter portion comprising residual stresses, surface tensions, or both that cause the filter portion to form a predetermined shape when the filter portion exits from the distal end of the thrombectomy catheter;
    positioning the filter portion of the thrombectomy filter wire downstream from the blood clot;
    securing the proximal end of the length of wire directly to a fixation device and securing the fixation device to a patient using a separate medical dressing in in order to secure the length of wire to the patient after the filter portion is positioned;
    applying a vacuum to the side passage to remove the blood clot through the thrombectomy catheter;
    detaching the length of wire from the fixation device; and
    removing the thrombectomy filter wire through the catheter including the filter portion and then removing the thrombectomy catheter.

2. The method of claim 1, wherein the thrombectomy filter wire further comprises a beaded element disposed towards the distal end of the length of wire proximally from the filter portion; and the method further comprises pulling portions of the clot into the thrombectomy catheter via the beaded element.

3. The method of claim 1, wherein the fixation device comprises a base portion and a protrusion extending outwardly from the base portion, and wherein the base portion is configured to be secured directly to the patient.

4. The method of claim 1, wherein the length of wire has a predetermined shape different than the predetermined shape of the filter portion.

5. A thrombectomy filter wire comprising:
    a length of wire having a proximal end and a distal end, the length of wire being configured to deploy through a thrombectomy catheter, the proximal end being configured to manipulate the length of wire when the length of wire is deployed; and
    a filter portion disposed on the distal end of the length of wire, the filter portion comprising residual stresses, surface tensions, or both that cause the filter portion to form a predetermined shape when the filter portion exits from a distal end of the thrombectomy catheter;
    a fixation device configured to engage and be secured directly to the proximal end of the length of wire and to a patient after the filter portion is placed in the patient,
    wherein the fixation device comprises a base portion and a protrusion extending outwardly from the base portion, and wherein the base portion is configured to be secured directly to the patient, wherein the length of wire has a predetermined shape different than the predetermined shape of the filter portion, and wherein the fixation device is configured to engage and be secured directly to the proximal end of the length of wire without being directly or indirectly coupled to the thrombectomy catheter.

6. The thrombectomy filter wire of claim 5, further comprising a beaded element disposed towards the distal end of the length of wire proximally from the filter portion.

7. The thrombectomy filter wire of claim 5, wherein the predetermined shape of the filter portion comprises one of a helix shape, a vortex shape, a nested shape, and a tangled web shape.

8. The thrombectomy filter wire of claim 5, wherein the filter portion comprises a lumen and a permeable wall.

9. A thrombectomy filter wire and catheter system comprising:
- a thrombectomy catheter comprising a proximal end and a distal end, the proximal end comprising a luer lock;
- a thrombectomy filter wire comprising:
  - a length of wire having a proximal end and a distal end, the length of wire being configured to deploy through the thrombectomy catheter, the proximal end being configured to manipulate the length of wire when the length of wire is deployed; and
  - a filter portion disposed on the distal end of the length of wire, the filter portion comprising residual stresses, surface tensions, or both that cause the filter portion to form a predetermined shape when the filter portion exits from the distal end of the thrombectomy catheter wherein the length of wire comprises a lumen forming an internal passage to a permeable wall;
- a hub attachment configured to provide an opening to an access port into the internal passage of the length of wire and selectively provide a clamping or compression force to selectively open or close the opening of the internal passage to thereby control flow of medication in the internal passage; and
- a compression element disposed between the hub attachment and the luer lock, wherein movement of the luer lock with respect to the hub attachment crushes the compression element, and wherein the luer lock comprises an internally threaded outer ring that is threadably coupled to the hub attachment.

10. The system of claim 9, wherein the length of wire is configured to extend through the compression element.

11. The system of claim 9, wherein the thrombectomy filter wire further comprises a beaded element disposed towards the distal end of the length of wire proximally from the filter portion.

12. The system of claim 9, wherein the predetermined shape comprises one of a helix shape, a vortex shape, a nested shape, and a tangled web shape.

13. The system of claim 9, wherein the filter portion comprises a lumen and a permeable wall.

14. The system of claim 9, wherein the length of wire has a predetermined shape different than the predetermined shape of the filter portion.

* * * * *